(12) United States Patent
Liddy et al.

(10) Patent No.: US 9,510,934 B2
(45) Date of Patent: Dec. 6, 2016

(54) IMPLANTABLE MEDICAL DEVICE HAVING A SLEEVE

(71) Applicants: Alison Liddy, Galway (IE); Michael Ryan, Limerick (IE); Gerard Treacy, Limerick (IE); John Neilan, Galway (IE)

(72) Inventors: Alison Liddy, Galway (IE); Michael Ryan, Limerick (IE); Gerard Treacy, Limerick (IE); John Neilan, Galway (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 645 days.

(21) Appl. No.: 13/946,023

(22) Filed: Jul. 19, 2013

(65) Prior Publication Data

US 2014/0025158 A1  Jan. 23, 2014

Related U.S. Application Data

(60) Provisional application No. 61/673,837, filed on Jul. 20, 2012.

(51) Int. Cl.
*A61F 2/06* (2013.01)
*A61F 2/04* (2013.01)
*A61F 2/24* (2006.01)

(52) U.S. Cl.
CPC . *A61F 2/06* (2013.01); *A61F 2/04* (2013.01); *A61F 2/24* (2013.01); *A61F 2002/044* (2013.01)

(58) Field of Classification Search
CPC .............. A61F 2/06; A61F 2/04; A61F 2/24; A61F 2002/044
See application file for complete search history.

(56) References Cited

U.S. PATENT DOCUMENTS

| | | |
|---|---|---|
| 4,222,126 A | 9/1980 | Boretos et al. |
| 4,580,568 A | 4/1986 | Gianturco |
| 5,314,473 A | 5/1994 | Godin |
| 5,366,506 A | 11/1994 | Davis |
| 5,449,385 A | 9/1995 | Religa et al. |
| 5,876,448 A | 3/1999 | Thompson et al. |
| 6,013,102 A | 1/2000 | Pintauro et al. |
| 6,187,043 B1 | 2/2001 | Ledergerber |
| 6,206,931 B1 | 3/2001 | Cook et al. |
| 6,231,598 B1 | 5/2001 | Berry et al. |
| 6,254,642 B1 | 7/2001 | Taylor |
| 6,264,700 B1 | 7/2001 | Kilcoyne et al. |
| 6,299,604 B1 | 10/2001 | Ragheb et al. |

(Continued)

FOREIGN PATENT DOCUMENTS

| | | |
|---|---|---|
| WO | WO0156500 | 8/2001 |
| WO | WO0224119 | 3/2002 |

(Continued)

OTHER PUBLICATIONS

International Searching Authority, The International Search Report and the Written Opinion of the International Searching Authority for International Application No. PCT/US2013/051204, mailed Oct. 18, 2013, p. 1-9.

(Continued)

*Primary Examiner* — Julian W Woo
(74) *Attorney, Agent, or Firm* — Buchanan Nipper

(57) ABSTRACT

Implantable medical devices are described. For example, various implantable medical devices having a sleeve with differential wall thicknesses are described. An exemplary medical device comprises a frame and a sleeve that has a first configuration where the sleeve is in an extended position and a second configuration where the sleeve is in an inverted position.

20 Claims, 7 Drawing Sheets

(56) References Cited

U.S. PATENT DOCUMENTS

| | | |
|---|---|---|
| 6,299,635 B1 | 10/2001 | Frantzen |
| 6,358,284 B1 | 3/2002 | Fearnot et al. |
| 6,458,153 B1 | 10/2002 | Bailey et al. |
| 6,464,720 B2 | 10/2002 | Boatman et al. |
| 6,494,909 B2 | 12/2002 | Greenhalgh |
| 6,508,833 B2 | 1/2003 | Pavcnik et al. |
| 6,544,291 B2 | 4/2003 | Taylor |
| 6,558,429 B2 | 5/2003 | Taylor |
| 6,659,937 B2 | 12/2003 | Polsky et al. |
| 6,666,892 B2 | 12/2003 | Hiles et al. |
| 6,720,402 B2 | 4/2004 | Langer et al. |
| 6,746,489 B2 | 6/2004 | Dua et al. |
| 6,790,214 B2 | 9/2004 | Kraemer et al. |
| 6,921,378 B2 | 7/2005 | O'Keefe et al. |
| 6,974,474 B2 | 12/2005 | Pavcnik et al. |
| 7,001,431 B2 | 2/2006 | Bao et al. |
| 7,011,094 B2 | 3/2006 | Rapacki et al. |
| 7,044,981 B2 | 5/2006 | Liu et al. |
| 7,361,189 B2 | 4/2008 | Case et al. |
| 7,402,171 B2 | 7/2008 | Osborne et al. |
| 7,445,642 B2 | 11/2008 | Amos et al. |
| 7,503,928 B2 | 3/2009 | Case et al. |
| 7,520,894 B2 | 4/2009 | Pavcnik et al. |
| 7,524,332 B2 | 4/2009 | Osborne et al. |
| 7,544,205 B2 | 6/2009 | Flagle et al. |
| 7,569,071 B2 | 8/2009 | Haverkost et al. |
| 7,670,332 B2 | 3/2010 | O'Keefe et al. |
| 7,686,844 B2 | 3/2010 | Case et al. |
| 7,699,830 B2 | 4/2010 | Martin |
| 7,819,836 B2 | 10/2010 | Levine et al. |
| 7,942,887 B2 | 5/2011 | Kraemer et al. |
| 7,955,375 B2 | 6/2011 | Agnew |
| 7,993,410 B2 | 8/2011 | Shin et al. |
| 8,029,557 B2 * | 10/2011 | Sobrino-Serrano ....... A61F 2/04 623/1.24 |
| 2001/0020189 A1 | 9/2001 | Taylor |
| 2001/0020190 A1 | 9/2001 | Taylor |
| 2001/0039450 A1 | 11/2001 | Pavcnik et al. |
| 2001/0041928 A1 | 11/2001 | Pavcnik et al. |
| 2003/0040808 A1 | 2/2003 | Stack et al. |
| 2003/0229366 A1 * | 12/2003 | Reggie ................. A61B 1/3137 606/158 |
| 2004/0044407 A1 | 3/2004 | Verona et al. |
| 2004/0102855 A1 | 5/2004 | Shank |
| 2004/0106976 A1 | 6/2004 | Bailey et al. |
| 2004/0117004 A1 | 6/2004 | Osborne et al. |
| 2004/0117031 A1 | 6/2004 | Stack et al. |
| 2004/0158331 A1 | 8/2004 | Stack et al. |
| 2004/0172141 A1 | 9/2004 | Stack et al. |
| 2004/0225352 A1 | 11/2004 | Osborne et al. |
| 2004/0243222 A1 | 12/2004 | Osborne et al. |
| 2005/0085900 A1 | 4/2005 | Case et al. |
| 2005/0154405 A1 | 7/2005 | Kraemer et al. |
| 2005/0187565 A1 | 8/2005 | Baker et al. |
| 2005/0187614 A1 | 8/2005 | Agnew |
| 2005/0228505 A1 | 10/2005 | Cornet et al. |
| 2005/0234546 A1 | 10/2005 | Nugent et al. |
| 2006/0041319 A1 | 2/2006 | Taylor et al. |
| 2006/0106454 A1 | 5/2006 | Osborne et al. |
| 2006/0116548 A1 | 6/2006 | Case et al. |
| 2006/0235511 A1 | 10/2006 | Osborne |
| 2006/0259128 A1 | 11/2006 | Pavcnik et al. |
| 2006/0265053 A1 | 11/2006 | Hunt |
| 2007/0016306 A1 | 1/2007 | Dua et al. |
| 2007/0027549 A1 | 2/2007 | Godin |
| 2007/0112437 A1 | 5/2007 | Shank |
| 2007/0129738 A1 | 6/2007 | Kraemer et al. |
| 2007/0162057 A1 | 7/2007 | Kraemer et al. |
| 2007/0162058 A1 | 7/2007 | Kraemer et al. |
| 2007/0167961 A1 | 7/2007 | Kraemer et al. |
| 2007/0208429 A1 | 9/2007 | Leahy |
| 2007/0260327 A1 | 11/2007 | Case et al. |
| 2008/0200936 A1 | 8/2008 | Kraemer et al. |
| 2008/0200937 A1 | 8/2008 | Kraemer et al. |
| 2008/0208215 A1 | 8/2008 | Kraemer et al. |
| 2008/0228206 A1 | 9/2008 | Kraemer et al. |
| 2008/0228285 A1 | 9/2008 | Kraemer et al. |
| 2008/0249538 A1 | 10/2008 | Kraemer et al. |
| 2008/0275470 A1 | 11/2008 | Kraemer et al. |
| 2008/0281337 A1 | 11/2008 | Kraemer et al. |
| 2008/0287966 A1 | 11/2008 | Kraemer et al. |
| 2009/0105813 A1 | 4/2009 | Chambers et al. |
| 2009/0118712 A1 | 5/2009 | Carter et al. |
| 2010/0023114 A1 | 1/2010 | Chambers et al. |
| 2010/0121461 A1 | 5/2010 | Sobrino-Serrano et al. |
| 2010/0121462 A1 | 5/2010 | Sobrino-Serrano et al. |
| 2010/0137998 A1 | 6/2010 | Sobrino-Serrano et al. |
| 2011/0054497 A1 | 3/2011 | Kraemer et al. |
| 2011/0087198 A1 | 4/2011 | Carter et al. |
| 2011/0087337 A1 | 4/2011 | Forsell |
| 2011/0160836 A1 | 6/2011 | Behan |
| 2011/0190796 A1 | 8/2011 | Kraemer et al. |
| 2011/0190905 A1 | 8/2011 | Behan |
| 2011/0202078 A1 | 8/2011 | Kraemer et al. |

FOREIGN PATENT DOCUMENTS

| | | |
|---|---|---|
| WO | WO0241764 | 5/2002 |
| WO | WO2004080352 | 9/2004 |
| WO | WO2005032422 | 4/2005 |
| WO | WO2006125055 | 11/2006 |

OTHER PUBLICATIONS

International Searching Authority, "International Preliminary Report on Patentability," for International Application No. PCT/US2013/051204, mailed on Jan. 29, 2015, pp. 1-7.

European Patent Office, The International Search Report and the Written Opinion of the International Searching Authority, Feb. 1, 2010, International Application No. PCT/US2009/051612.

International Preliminary Report on Patentability, The International Bureau of WIPO, Feb. 3, 2011, for International Application No. PCT/US2009/051612.

* cited by examiner

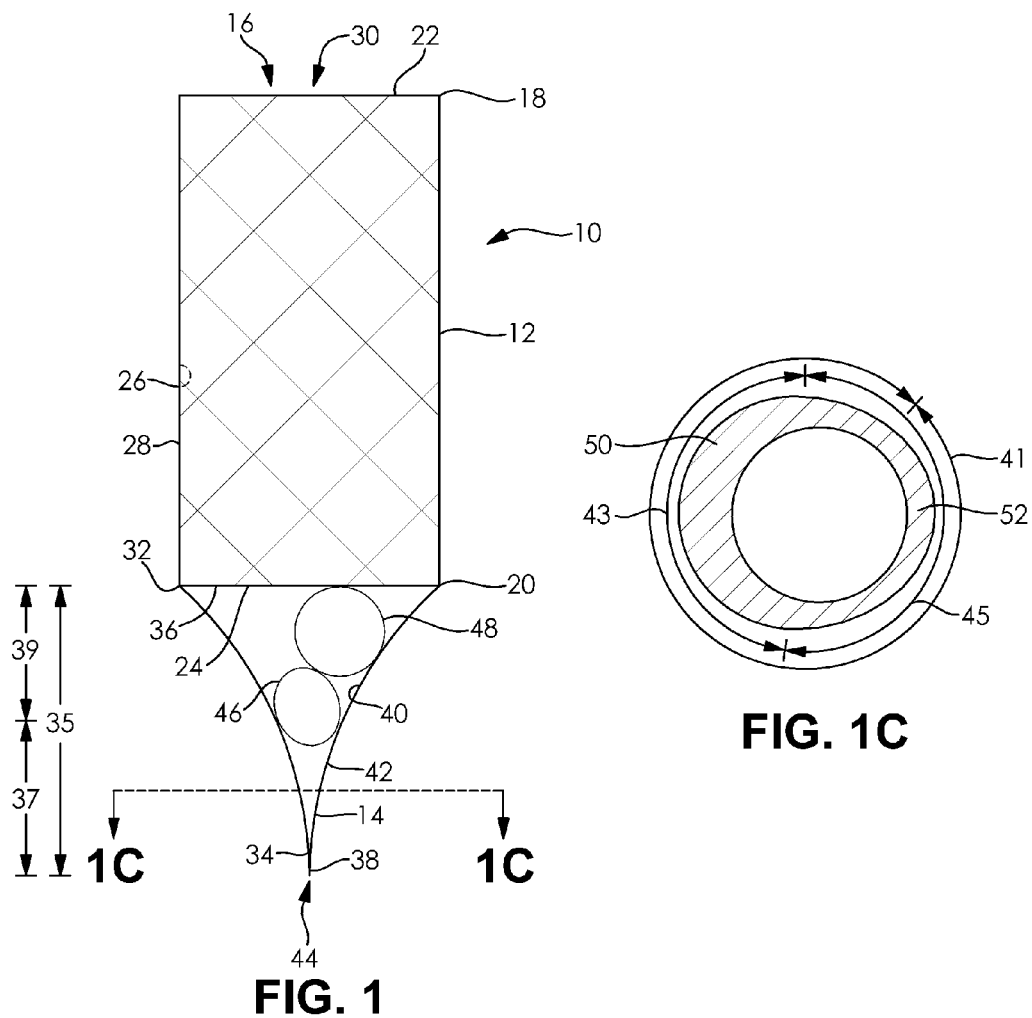
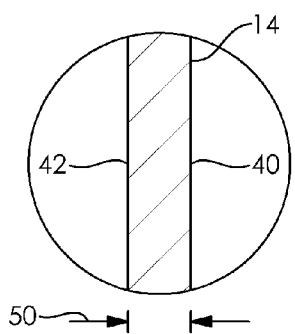
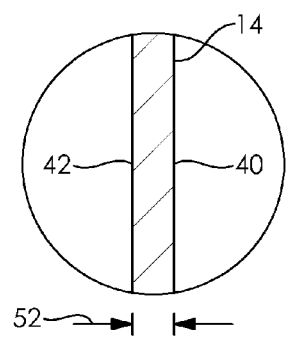

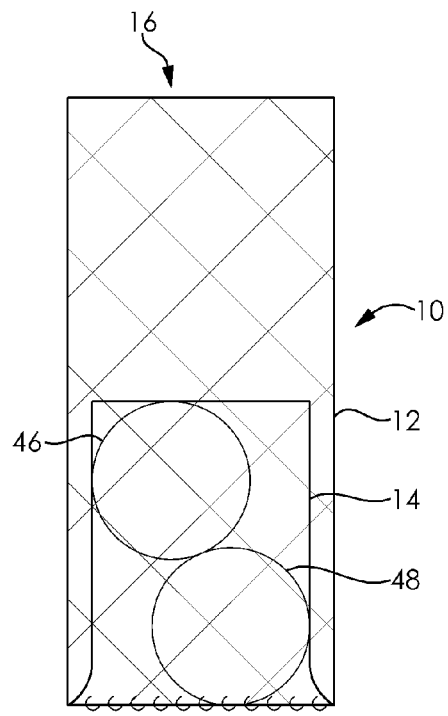
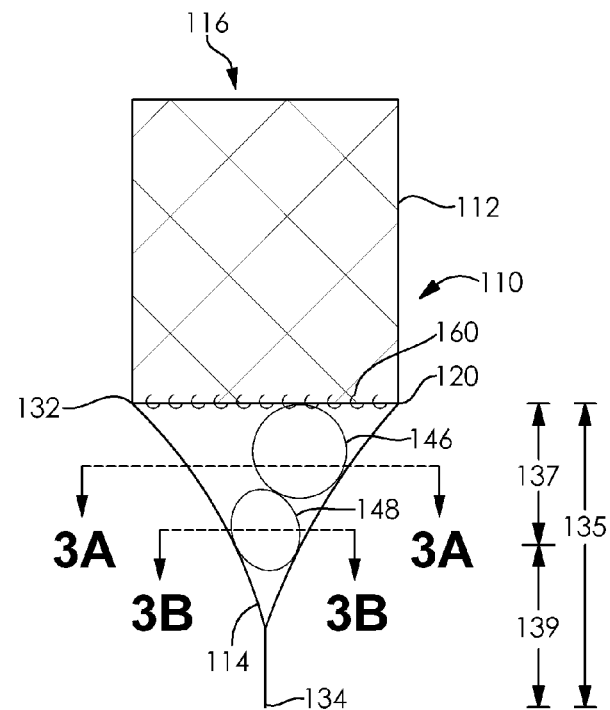
FIG. 2          FIG. 3
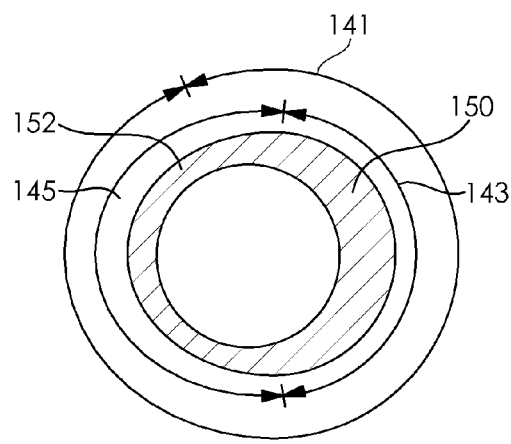
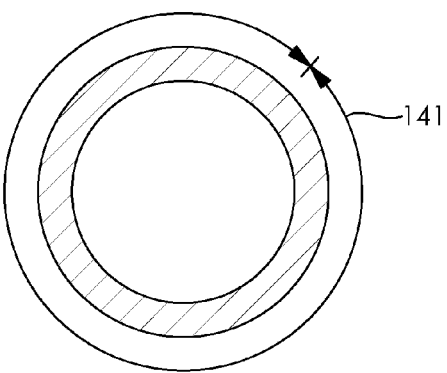
FIG. 3A          FIG. 3B

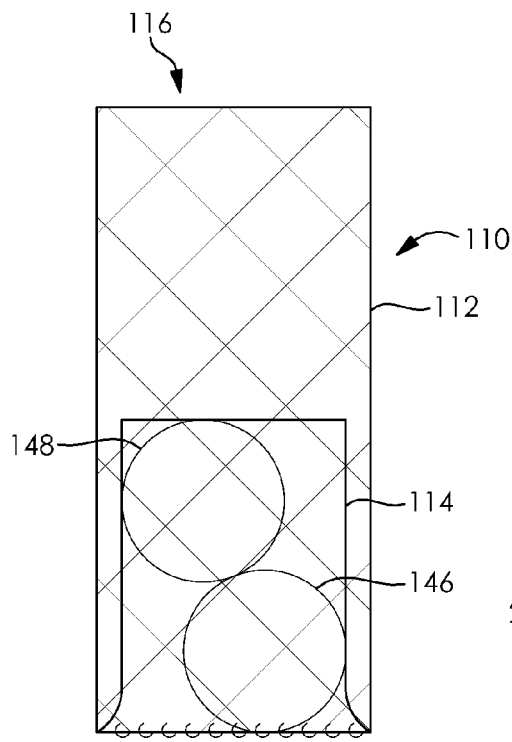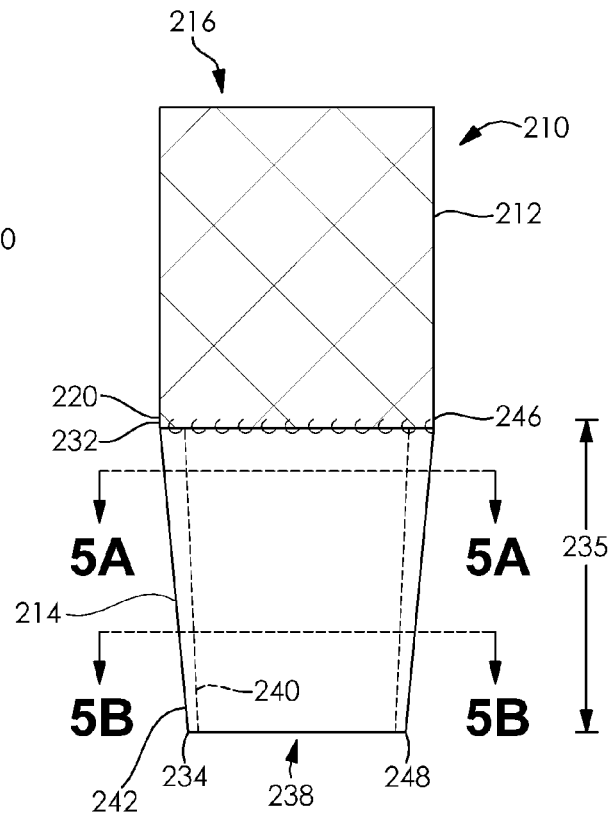
FIG. 4   FIG. 5
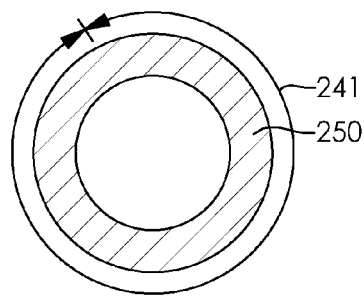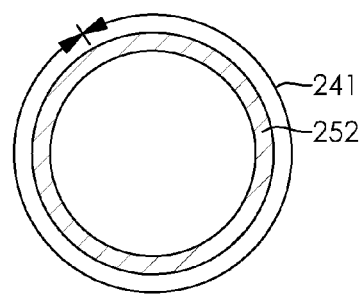
FIG. 5A   FIG. 5B

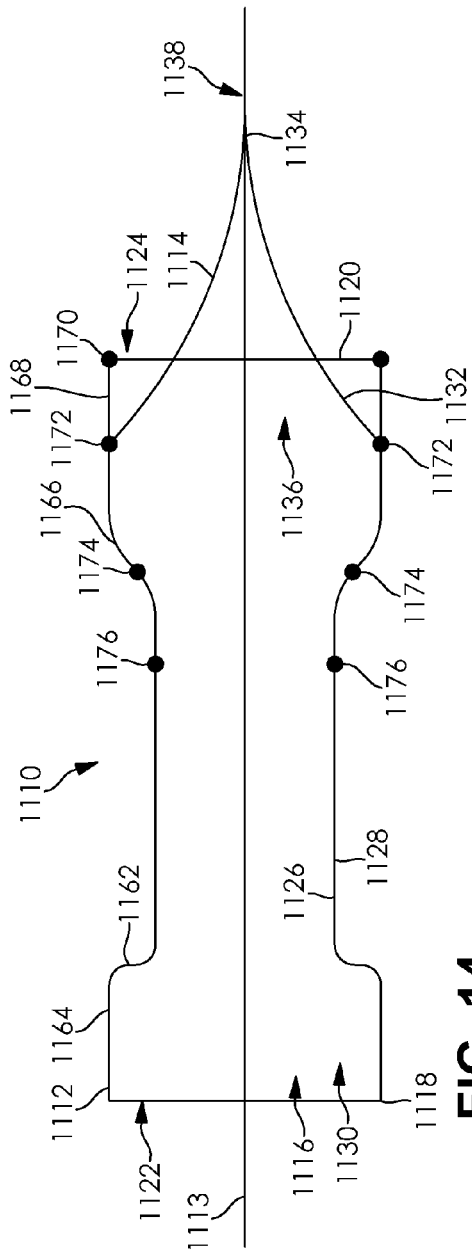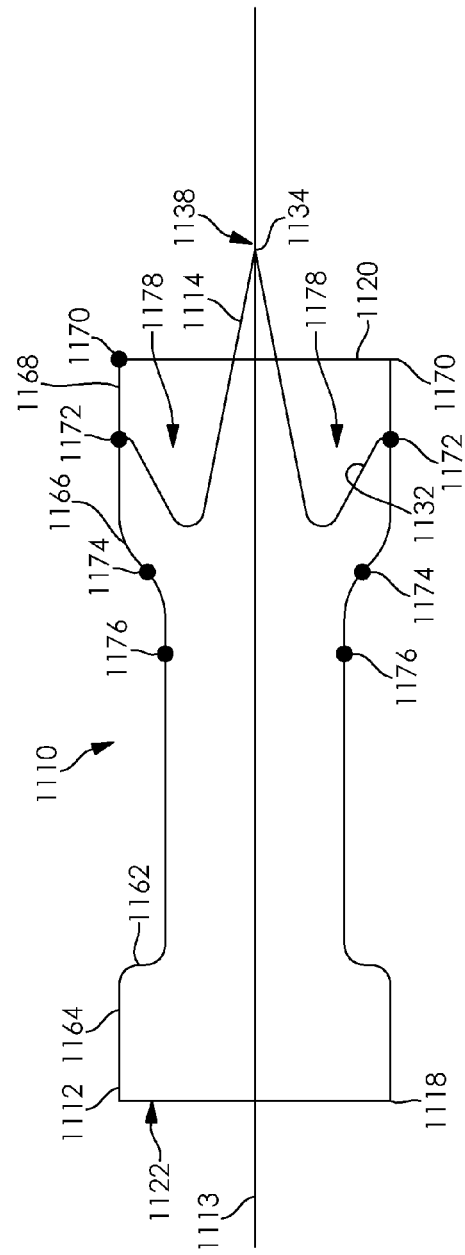

IMPLANTABLE MEDICAL DEVICE HAVING A SLEEVE

FIELD

The disclosure relates generally to medical devices. More particularly, the disclosure relates to implantable medical devices having a sleeve.

BACKGROUND

Minimally invasive techniques and instruments for placement of intraluminal medical devices have developed over recent years. A wide variety of treatment devices that utilize minimally invasive technology have been developed and include stents, stent grafts, occlusion devices, infusion catheters and the like. Stents—frame-like structures placed within a body vessel to provide support to and maintain patency of the vessel—became especially popular with the introduction of coronary stents to the U.S. market in the early 1990s. Since that time, both coronary and peripheral stents have been proven to provide a superior means of maintaining vessel patency, and have become widely accepted in the medical community.

The use of stents has been extended to treatments that target other body vessels. For example, bile duct stents, ureter stents, and esophageal stents are now widely used to maintain patency of each of these bodily passages. Esophageal stents, for example, are sometimes used to maintain patency of the esophagus from a point within the vessel, such as in the treatment of a stricture that threatens closure of this vessel.

Stenting of the esophagus provides unique challenges not faced by stents intended for other vessels, such as vessels of the vasculature. For example, the lower esophageal sphincter—a muscle near the junction with the stomach—is normally closed to block stomach acid from entering the esophagus. Normally, this muscle only opens during swallowing to allow food to pass into the stomach. After a stent is placed across this muscle, however, the sphincter can remain open in response to the intraluminal support provided by the stent, reducing the ability of the muscle to block acid entry into the esophagus. Over time, acid passage into the esophagus can cause tissue damage, aspiration pneumonia, and other undesirable outcomes.

Thus, a need exists for improved medical devices for modifying the flow of material and/or fluid through a bodily passage.

SUMMARY

Various exemplary intraluminal medical devices are described.

A first exemplary intraluminal medical device comprises an expandable frame and a sleeve. The expandable frame has a first frame end and a second frame end and defines a frame lumen that extends from the first frame end to the second frame end. The sleeve is attached to the frame and has a first sleeve end, a second sleeve end, an inner surface, an outer surface, a first portion, a second portion, a circumferential length, and an axial length. The sleeve defines a sleeve lumen that extends between the first sleeve end and the second sleeve end and the axial length of the sleeve extends from the first sleeve end to the second sleeve end. The first portion extends along a portion of the circumferential length and a portion of the axial length from the first sleeve end towards the second sleeve end. The first portion has a first wall thickness that extends between the inner surface and the outer surface. The second portion extends along a portion of the circumferential length and a portion of the axial length from the second sleeve end towards the first sleeve end. The second portion has a second wall thickness that extends between the inner surface and the outer surface. The first wall thickness is greater than the second wall thickness. The sleeve is adapted to invert between an extended position in which the second sleeve end and a part of the first portion is disposed outside of the frame lumen and an inverted position in which the second sleeve end and the part of the first portion is disposed within the frame lumen.

A second exemplary intraluminal medical device comprises an expandable frame and a sleeve. The expandable frame has a first frame end and a second frame end and defines a frame lumen that extends from the first frame end to the second frame end. The sleeve has a first sleeve end attached to the frame, a second sleeve end, an inner surface, an outer surface, a first portion, a second portion, a circumferential length, and an axial length. The sleeve defines a sleeve lumen that extends between the first sleeve end and the second sleeve end and the axial length of the sleeve extends from the first sleeve end to the second sleeve end. The first portion extends along a portion of the circumferential length and a portion of the axial length from the first sleeve end towards the second sleeve end. The first portion has a first wall thickness that extends between the inner surface and the outer surface. The second portion extends along a portion of the circumferential length and a portion of the axial length from the second sleeve end towards the first sleeve end. The second portion has a second wall thickness that extends between the inner surface and the outer surface. The first wall thickness is greater than the second wall thickness and the sleeve defines a taper between the first sleeve end and the second sleeve end along a portion of the axial length. The sleeve is adapted to invert between an extended position in which the second sleeve end and a part of the first portion is disposed outside of the frame lumen and an inverted position in which the second sleeve end and the part of the first portion is disposed within the frame lumen.

A third exemplary intraluminal medical device comprises an expandable frame and a sleeve. The expandable frame has a first frame end and a second frame end and defines a frame lumen that extends from the first frame end to the second frame end. The sleeve has a first sleeve end attached to the frame, a second sleeve end, an inner surface, an outer surface, a first portion, a second portion, a circumferential length, and an axial length. The sleeve defines a sleeve lumen that extends between the first sleeve end and the second sleeve end and the axial length of the sleeve extends from the first sleeve end to the second sleeve end. The first portion extends along the entire circumferential length and a portion of the axial length from the first sleeve end towards the second sleeve end. The first portion has a first wall thickness that extends between the inner surface and the outer surface. The second portion extends along the entire circumferential length and a portion of the axial length from the second sleeve end towards the first sleeve end. The second portion has a second wall thickness that extends between the inner surface and the outer surface. The first wall thickness is greater than the second wall thickness and the sleeve defines a continuous taper between the first sleeve end and the second sleeve end. The sleeve is adapted to invert between an extended position in which the second sleeve end and a part of the first portion is disposed outside of the frame lumen and an inverted position in which the second sleeve end and the part of the first portion is disposed within the frame lumen.

Additional understanding of the exemplary medical devices can be obtained by review of the detailed description, below, and the appended drawings.

BRIEF DESCRIPTION OF THE FIGURES

FIG. 1 is a side view of a first exemplary intraluminal medical device. The intraluminal medical device is shown in a first configuration.

FIG. 1A is a sectional view of a first portion of the sleeve of the intraluminal medical device illustrated in FIG. 1.

FIG. 1B is a sectional view of a second portion of the sleeve of the intraluminal medical device illustrated in FIG. 1.

FIG. 1C is a sectional view of the intraluminal medical device illustrated in FIG. 1, taken along line 1C-1C.

FIG. 2 is a side view of the first exemplary intraluminal medical device in a second configuration.

FIG. 3 is a side view of a second exemplary intraluminal medical device. The intraluminal medical device is shown in a first configuration.

FIG. 3A is a sectional view of the intraluminal medical device illustrated in FIG. 3, taken along line 3A-3A.

FIG. 3B is a sectional view of the intraluminal medical device illustrated in FIG. 3, taken along line 3B-3B.

FIG. 4 is a side view of the second exemplary intraluminal medical device in a second configuration.

FIG. 5 is a side view of a third exemplary intraluminal medical device. The intraluminal medical device is shown in a first configuration.

FIG. 5A is a sectional view of the intraluminal medical device illustrated in FIG. 5, taken along line 5A-5A.

FIG. 5B is a sectional view of the intraluminal medical device illustrated in FIG. 5, taken along line 5B-5B.

FIG. 14 is a side view of a fourth exemplary intraluminal medical device. The intraluminal medical device is shown in a first configuration.

FIG. 15 is a side view of the fourth exemplary intraluminal medical device between the first configuration and a second configuration.

DETAILED DESCRIPTION

Figure 6:
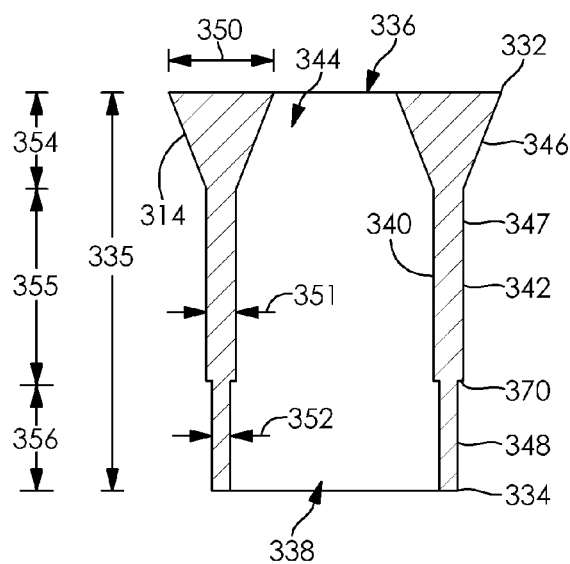
FIG. 6 is a sectional view of an alternative sleeve for inclusion in an intraluminal medical device.

The following detailed description and the appended drawings describe and illustrate various exemplary medical devices. The description and drawings are exemplary in nature and are provided to enable one skilled in the art to make and use one or more exemplary device. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. As used herein, the terms "proximal" and "distal" are used to describe opposing axial ends of the particular elements or features being described. The use of "bodily passage" or "body passage" refers to any passage within the body of an animal, including, but not limited to, humans, and includes elongate passages. The use of "exemplary" refers to "an example of" and is not intended to convey a meaning of an ideal or preferred embodiment. The use of "circumferential" refers to the distance around the particular element or feature being described and is not intended to define any particular geometric shape.

FIGS. 1, 1A, 1B, 1C, and 2 illustrate a first exemplary intraluminal medical device 10. The intraluminal medical device 10 comprises a frame 12 and a sleeve 14 attached to the frame 12. The frame 12 and sleeve 14 cooperatively define a device lumen 16 that extends through the length of the intraluminal medical device 10.

Frame 12 can comprise any suitable frame, and skilled artisans will be able to select a suitable frame according to a particular embodiment based on various considerations, including the bodily passage within which the device is intended to be used. Example frames considered suitable include, but are not limited to, expandable, self-expandable, and frames that require the application of a force to effect expansion, such as balloon expandable frames. The structural characteristics of these types of frames are known in the art, and are not detailed herein.

Frame 12 can be formed of any suitable material and have any suitable proportions. A skilled artisan will be able to select a suitable material and suitable proportions for a frame based on various considerations, including the bodily passage within which the device is intended to be used. The material selected for a frame need only be biocompatible or able to be made biocompatible. Example materials considered suitable include, without limitation, stainless steel, nickel titanium (NiTi) alloys, e.g., nitinol, other shape memory and/or superelastic materials, molybdenum alloys, tantalum alloys, titanium alloys, palladium alloys, precious metals such as platinum, precious metal alloys such as platinum alloys, nickel chromium alloys, cobalt chromium alloys, nickel cobalt chromium alloys, nickel cobalt chromium molybdenum alloys, nickel titanium chromium alloys, linear elastic Nitinol wires, polymers, and composite materials. The inventors have determined that frames having a length between about 2 cm and about 18 cm are considered suitable. In addition, the inventors have determined that frames having a diameter between about 1 mm to about 30 mm are considered suitable.

A number of resorbable materials also can be used to form a frame. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethylene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein. Absorbable metals and minerals, such as magnesium and calcium, are also considered suitable.

Bioremodellable materials also can be used to form a frame. As used herein, the term "bioremodellable" refers to the ability of a material to remodel and become incorporated into adjacent tissues. These materials can provide a scaffold onto which cellular in-growth can occur, eventually allowing the material to remodel into a structure of host cells. A number of bioremodellable materials are known in the art, and any suitable bioremodellable material can be used. Examples of suitable bioremodellable materials include extracellular matrix (ECM) materials, such as small intestine submucosa (SIS), bovine pericardium, stomach submucosa, liver basement membrane, urinary bladder submucosa, tissue mucosa, and dura mater.

Platinum and nitinol are currently considered desirable materials for use in the frame 12 due at least to their biocompatibility, shapeability, imaging characteristics, and well-characterized nature. Stainless steel is also considered a suitable material for use in the frame 12. Also, cold drawn cobalt chromium alloys, such as AS™ F562 and AS™ F1058 (commercial examples of which include MP35N™ and Elgiloy™, both of which are available from Fort Wayne Metals, Fort Wayne, Ind.; MP35N is a registered trademark of SPS Technologies, Inc. (Jenkintown, Pa., USA); Elgiloy is a registered trademark of Combined Metals of Chicago LLC (Elk Grove Village, Ill., USA)), are currently considered advantageous materials for use in the frame 12 at least because they are non-magnetic materials that provide beneficial magnetic resonance imaging (MRI) compatibility, and avoid MRI artifacts typically associated with some other materials, such as stainless steel.

Frame 12 can optionally include a covering disposed around a portion, or the entirety, of the circumferential length and/or axial length of the frame. Any suitable covering can be included in any of the intraluminal medical devices describer herein, and skilled artisans will be able to select a suitable covering for an intraluminal medical device according to a particular embodiment based on various considerations, including the desired bodily passage within which the intraluminal medical device is intended to be deployed. If included, a covering need only be able to be attached or otherwise connected to the frame of an intraluminal medical device.

A covering comprises a section of material, such as a sheet, that is attached to the frame of an intraluminal medical device. The covering can be formed of any suitable material, and skilled artisans will be able to select a suitable material to form a covering according to a particular embodiment based on various considerations, including the desired bodily passage within which the intraluminal medical device is intended to be deployed. Example materials considered suitable to form a covering include, but are not limited to, biocompatible materials, materials that can be made biocompatible, flexible materials, natural materials, synthetic materials, combinations of natural materials and synthetic materials, any suitable material described herein, and any other material considered suitable for a particular application. Examples of suitable natural materials include, but are not limited to, extracellular matrix (ECM) materials, such as small intestine submucosa (SIS), and other bioremodellable materials, such as bovine pericardium. Other examples of ECM materials that can be used include stomach submucosa, liver basement membrane, urinary bladder submucosa, tissue mucosa, and dura matter. Examples of suitable synthetic materials include polymeric materials, such as expanded polytetrafluoroethylene and polyurethane. ECM materials are considered suitable to form covering at least because of their abilities to remodel and become incorporated into adjacent tissues, facilitating anchoring of an intraluminal medical device at a point of treatment in a body passage. These materials can provide a scaffold onto which cellular in-growth can occur, eventually allowing the material to remodel into a structure of host cells. It is noted that two or more different materials can be used to form the covering.

The covering can be attached to the frame in any suitable manner and using any suitable means for attaching a covering to a frame, such as sutures, clips, and other mechanical attachment elements. Alternatively, bonding agents and/or techniques can be used, such as adhesives, heat sealing, tissue welding, and cross-linking. Furthermore, direct attachment of the covering to the frame can be used. For example, the struts of the frame can be woven through the covering to create an attachment. Also, the frame can be embedded within the covering, such as by dipping and spraying a polymeric material onto the frame to form an attached covering. The specific manner in which a particular covering is attached to an intraluminal medical device will depend at least upon the materials used in the covering and the frame. Example methods of attaching a covering to a frame include, but are not limited to, attaching a covering to an inner frame surface along a portion, or the entirety, of the circumferential length and/or axial length of the frame, attaching a covering to an outer frame surface along a portion, or the entirety, of the circumferential length and/or axial length of the frame, dipping and/or spraying a portion, or the entirety, of the circumferential length and/or axial length of a frame with a covering material, attaching a covering to an inner frame surface along a portion, or the entirety, of the circumferential length and/or axial length of the frame and dipping and/or spraying a portion, or the entirety, of the circumferential length and/or axial length of the frame with a covering material, and attaching a covering to an outer frame surface along a portion, or the entirety, of the circumferential length and/or axial length of the frame and dipping and/or spraying a portion, or the entirety, of the circumferential length and/or axial length of the frame with a covering material.

Frame 12 can have a variety of shapes and structural arrangements, including braided strands, helically wound strands, ring members, consecutively attached ring members, zig-zag members, tubular members, frames cut from solid tubes, and solid tubular members. A skilled artisan will be able to select a suitable shape and structural arrangement for a frame according to a particular embodiment based on various considerations, such as the bodily passage within which the device is intended to be used. Frames for use in the intraluminal medical devices described herein can be formed in a variety of manners. For example, a frame can be formed from one or more wires, such as from lengths of wire having a circular, D-shaped or other suitable cross-sectional configuration. Also, a frame can be cut from a tubular member, such as by cutting a desired pattern of struts from a tubular section of a suitable material. No matter the type of frame used in an intraluminal medical device according to a particular embodiment, the frame can include any suitable arrangement of struts.

In the illustrated embodiment, frame 12 comprises a self-expandable wire mesh frame with a plurality of intersecting wire portions and a plurality of mesh openings. The frame 12 has a first frame end 18 and a second frame end 20. The first frame end 18 defines a first frame end opening 22 and the second frame end 20 defines a second frame end opening 24. The frame 12 has inner frame surface 26 and an outer frame surface 28 and defines a frame lumen 30 that extends from the first frame end 18 to the second frame end 20.

Sleeve 14 can comprise any suitable member having any suitable structural arrangement, and skilled artisans will be able to select a suitable member and structural arrangement according to a particular embodiment based on various considerations, including the bodily passage within which the device is intended to be used. Example structural arrangements considered suitable for a sleeve include, but are not limited to, tubular, a sleeve with a proximal portion having a first configuration and a distal portion with a second, different, configuration, and a sleeve having multiple structural configurations along its axial length and/or circumferential length. For example, a sleeve can have a first portion that extends from the proximal end of the sleeve towards the distal end that has a first tubular and/or cylindrical configuration and a second portion that extends from the distal end towards the proximal end that has a second, different, configuration. The second portion can comprise any suitable configuration. Example configurations considered suitable for the second portion of a sleeve include, but are not limited to, cylindrical, beak-shaped, tricuspid-shaped, cone-shaped, tapered, rectangular, square, semi-circular, chisel-shaped, hemi-spherical, curved (e.g., axial view is configured like a smile), and spherical. Sleeve 14 need only be adapted to be invertible into the frame lumen 30, partially invertible into the frame lumen 30, or non-invertible, as described herein.

Sleeve 14 can be formed of any suitable material, and skilled artisans will be able to select a suitable material for a sleeve according to a particular embodiment based on various considerations, including the bodily passage within which the device is intended to be used. The material selected for a sleeve need only be biocompatible or able to be made biocompatible. Examples of suitable materials include, polymers, shape memory polymers, polytetrafluoroethylene (PTFE), elastomeric PTFE, polyurethane, shape memory polyurethane, polyethylene, UHMW polyethylene, elastomeric polyethylene, low density (LD) polyethylene, high density (HD) polyethylene, polypropylene, polyethylene terephthalate (PET), polyethyleneoxide (PEO), block copolymers containing polystyrene and poly(1,4-butadiene), an ABA triblock copolymer made from poly(2-methyl-2-oxazoline) and polytetrahydrofuran, amorphous or organic-inorganic hybrid polymers consisting of polynorbornene units, and poly-silicone.

In the illustrated embodiment, sleeve 14 is a tubular member having a first sleeve end 32, a second sleeve end 34, an axial length 35 that extends from the first sleeve end 32 to the second sleeve end 34, and a circumferential length 41, as illustrated in FIG. 1C. The first sleeve end 32 is attached to the second frame end 20 by dipping the second frame end 20 into the material forming sleeve 12. The first sleeve end 32 defines a first end opening 36 and the second sleeve end 34 defines a second end opening 38. The sleeve 14 has an inner sleeve surface 40 and an outer sleeve surface 42 and defines a sleeve lumen 44 that extends from the first sleeve end 32 to the second sleeve end 34.

The second sleeve end 34 is adapted to have a first configuration, as illustrated in FIG. 1, and a second configuration, as illustrated in FIG. 2. In the first configuration, the second end opening 38 is sealed, or substantially sealed, along a portion, or the entirety, of the circumferential length 41 such that materials (e.g., food) and/or fluids (e.g., water) are prevented from passing through the second end opening 38. In the second configuration, the second end opening 38 is open such that materials and/or fluid can pass through the second end opening 38. Second sleeve end 34 is adapted to be in the first configuration in which the second end opening 38 is sealed, or substantially sealed, under normal pressures in the bodily passage within which the intraluminal medical device is disposed.

The inventors have determined that the seal created on the sleeve second end is directly correlated with the thickness of the sleeve. For example, a sleeve having a first wall thickness on the second sleeve end will create a greater seal as compared to a sleeve having a second wall thickness on the sleeve second end that is greater than the first wall thickness. Thus, a greater seal can be accomplished by using a thinner wall thickness at the sleeve send end, or any portion thereof. The inventors have also determined that the shape of the sleeve second end also affects the extent at which a seal is created.

Sleeve 14 can have any suitable axial length and circumferential length, and skilled artisans will be able to select a suitable axial length and circumferential length for a sleeve according to a particular embodiment based on various considerations, including the desired amount of flexibility of the sleeve. The inventors have determined that a sleeve having an axial length between about 1 mm to about 70 mm is considered suitable. The inventors have also determined that a sleeve having an axial length between about 20 mm to about 45 mm is considered suitable.

Sleeve 14 has a first portion 46 and a second portion 48. The first portion 46 of the sleeve 14 extends from the second sleeve end 34 towards the first sleeve end 32 along a first portion 37 of the axial length 35 of the sleeve 14 and along a first portion 43 of the circumferential length 41 of the sleeve 14, as illustrated in FIG. 1C. The second portion 48 of the sleeve 14 extends from the first sleeve end 32 towards the second sleeve end 34 along a second portion 39 of the axial length 35 of the sleeve 14 and along the circumferential length 41 of the sleeve 14. Along the first portion 37 of the axial length 35 of the sleeve, the second portion 48 extends along a second portion 45 of the circumferential length 41 of the sleeve 14, as illustrated in FIG. 1C.

As best illustrated in FIG. 1A, the first portion 46 has a first wall thickness 50 that extends from the outer sleeve surface 42 to the inner sleeve surface 40. As best illustrated in FIG. 1B, the second portion 48 has a second wall thickness 52 that extends from the inner sleeve surface 40 to the outer sleeve surface 42. Thus, the second wall thickness 52 of the sleeve 14 is disposed at the point of attachment to frame 12. The first wall thickness 50 is different from the second wall thickness 52. In the illustrated embodiment, the first wall thickness 50 is greater than the second wall thickness 52.

The differential wall thicknesses 50, 52 can vary along the axial length 35 and/or the circumferential length of sleeve 14, and skilled artisans will be able to select suitable differential wall thicknesses for a sleeve according to a particular embodiment based on various considerations, including the desired flexibility of the sleeve. The inventors have determined that wall thicknesses between about 0.00254 mm and about 1.016 mm are considered suitable.

While differential wall thicknesses 50, 52 have been described, a sleeve can have any suitable wall thickness along the entirety, or a portion, of the axial length and/or circumferential length of the sleeve, and skilled artisans will be able to select a suitable wall thickness for the entirety, or a portion, of the axial length and/or circumferential length of a sleeve according to a particular embodiment based on various considerations, including the desired flexibility of the sleeve. Example structural arrangement considered suitable include, but are not limited to, a continuous wall thickness along the entire length of the sleeve, a varying wall thickness along the length of the sleeve (e.g., a first portion of the axial length and/or circumferential length having a first wall thickness and a second portion of the axial length and/or circumferential length having a second, different, wall thickness), a gradual increase in the wall thickness from the first sleeve end to the second sleeve end, a gradual decrease in the wall thickness from the first sleeve end to the second sleeve end, and a sleeve having a first portion disposed between the first sleeve end and the second sleeve end that has a greater wall thickness than the wall thickness at the first sleeve end and the second sleeve end.

Sleeve 14 can be formed using any suitable technique to achieve desired differential wall thicknesses 50, 52, and skilled artisans will be able to select a suitable technique to form a sleeve according to a particular embodiment based on various considerations, including the desired flexibility of the sleeve. Example techniques considered suitable to form a sleeve include, but are not limited to, dipping or spraying a mandrel formed of PTFE with one or more coats of a polymer to achieve desired differential wall thicknesses either before or after attachment of a sleeve to a frame. For example, a sleeve can be formed by applying one or more polymer coats (e.g., dipping, spraying) to the surface of a mandrel formed of PTFE. By isolating areas of the mandrel during the coating process, a sleeve can be coated to tailor fit the design requirements of a particular sleeve (e.g., a first portion having a thickness greater than a second portion). The greater number of polymer coats applied to the mandrel, the thicker the wall of a sleeve. Further examples of techniques considered suitable to achieve desired differential wall thicknesses included, but are not limited to, forming a sleeve, or portions thereof, of a laminate or of a unitary structure. Other methods considered suitable to form a sleeve include, but are not limited to, blow molding, casting, extruding, electrospinning, heat forming, spraying, weaving, knitting, and braiding.

In the illustrated embodiment, sleeve 14 is adapted to move between an extended position in which the second end 34 and a part of the second portion 48 are disposed outside of the frame lumen 30 to an inverted position in which the second end 34 and the part of the second portion 48 are disposed within the frame lumen 30. The intraluminal medical device 10 is in a first configuration, illustrated in FIG. 1, when the sleeve 14 is in the extended position and in a second configuration, illustrated in FIG. 2, when the sleeve 14 is in the inverted position.

It is considered advantageous to attach the second portion 48 of the sleeve 14, which has a second wall thickness 52 that is less than the first wall thickness 50, to the frame 12 to control the amount of pressure required to move the sleeve 14 from an extended position to an inverted position, and vice versa. For example, the first sleeve end 32 having a second wall thickness 52 that is less than the first wall thickness 50 allows for the sleeve 14 to move from the extended position to the inverted position, and vice versa, with the application of a smaller amount of pressure as compared to a first sleeve end 32 having a first wall thickness 50.

While the first sleeve end 32 has been described and illustrated as attached to the second frame end 20, sleeve 14 can be attached to the frame 12 at any suitable location along the axial length of the frame 12. A skilled artisan will be able to select a particular location to attach a sleeve to a frame according to a particular embodiment based on various considerations, such as the bodily passage within which the device is intended to be used. Example locations considered suitable to attach a sleeve to a frame include, but are not limited to, attaching a portion, or the entirety, of a first sleeve end to a first frame end, attaching a portion, or the entirety, of a first sleeve end to a second frame end, and attaching a portion, or the entirety, of a first sleeve end at a location between a first frame end and a second frame end. Further example locations considered suitable to attach a sleeve to a frame include, but are not limited to, attaching a portion, or the entirety, of a sleeve to a first frame end, attaching a portion, or the entirety, of a sleeve to a second frame end, and attaching a portion, or the entirety, of a sleeve at a location between a first frame end and a second frame end.

The differential wall thicknesses 50, 52 can be positioned on the sleeve 14 in any suitable arrangement, and skilled artisans will be able to select a suitable arrangement for a particular embodiment based on various considerations, including the desired pressure at which a sleeve is to invert. Example arrangements considered suitable for positioning a first portion and a second portion on a sleeve include, but are not limited to, having a first portion that extends along a portion, or the entirety, of the axial length of a sleeve, a first portion that extends along a portion, or the entirety, of the circumferential length of a sleeve, a second portion that extends along a portion, or the entirety, of the axial length of a sleeve, a second portion that extends along a portion, or the entirety, of the circumferential length of a sleeve, a first portion that extends along a portion of the circumferential length of a sleeve and a second portion that extends along another portion of the circumferential length of the sleeve, and/or a first portion that extends along a portion of the axial length of a sleeve and a second portion that extends along another portion of the axial length of the sleeve. In addition, it is also considered suitable to include varying wall thicknesses (e.g., first wall thickness 50, second wall thickness 52) at one or more locations along the axial length and/or circumferential length of a sleeve. For example, on any planar section orthogonal to the lengthwise axis of the sleeve 14, the wall thickness can vary around the circumferential length 41 of the sleeve 14.

A sleeve, or a portion thereof (e.g., first sleeve end), can be attached to the frame using any suitable structure and/or method of attachment, and skilled artisans will be able to select a suitable structure and method for attaching a sleeve to a frame according to a particular embodiment based on various considerations, including the bodily passage within which the device is intended to be used. Example methods of attachment between the frame and sleeve considered suitable include, but are not limited to, any method capable of bonding and/or attaching a sleeve to a frame, or any portion thereof (e.g., covering of the frame), using sutures, adhesives (e.g., silicone adhesives), ultraviolet curing, bonding, dipping, spraying, heat welding, and mechanical methods of attachment (e.g., clips, rings). Alternatively, the sleeve can be created in conjunction with the membrane of the stent.

Optionally, the entirety, or portions of, the frame 12 and/or sleeve 14 can comprise certain materials that permit identification of the position and/or orientation of the intraluminal medical device 10, frame 12, and/or sleeve 14 within a body passage. The frame 12 and/or sleeve 14 can include one or more radiopaque markers, and/or be formed of a radiopaque material, to aid a user in positioning the intraluminal medical device 10, frame 12, and/or sleeve 14 in a body passage. For example, the sleeve 14 can be formed of a material that can be identified by X-ray by adding radiopaque ingredients to a base polymer, which is dipped and/or sprayed onto the sleeve 14 during manufacture. It is considered advantageous to include a radiopaque material in a portion, or the entirety, of sleeve 14 to allow a user to observe the sleeve 14 moving from an extended position to an inverted position, and vice versa.

The radiopaque material may be added in any fabrication method or absorbed into or sprayed onto the surface of the entirety, or a portion, of the frame 12 and/or sleeve 14. The degree of radiopacity contrast can be altered by the type and amount of material incorporated into the frame 12 and/or sleeve 14. Common radiopaque materials include barium sulfate, bismuth subcarbonate, and zirconium dioxide. Other radiopaque elements include cadmium, tungsten, gold, tantalum, bismuth, platinum, iridium, and rhodium. Radiopacity is typically determined by fluoroscope or x-ray film.

In use, the intraluminal medical device 10 can be preloaded into a delivery device with the sleeve 14 in the extended position or the inverted position. It is considered advantageous to load the intraluminal medical device 10 into a delivery device with the sleeve 14 in the inverted position at least because this configuration would reduce the clinical complications with introducing the intraluminal medical device 10 into a bodily passage. Subsequent to delivery, the sleeve 14 can be moved to the extended position by passing a material (e.g., food) and/or fluid (e.g., water) through the lumen 30 of the frame 12 and through the lumen 44 of the sleeve 14. In instances where the intraluminal medical device 10 includes radiopaque material, successful inversion of the sleeve from the inverted position to the extended position can be confirmed under X-ray.

Optionally, the sleeve 14 can be disposed within a dissolvable sleeve formed of biocompatible material to reduce the likelihood of self-adherence. The dissolvable sleeve need only be biocompatible and able to dissolve in the contents of the bodily passage (e.g., stomach). Skilled artisans will be able to select a suitable material to form the dissolvable sleeve according to a particular embodiment based on various considerations, including the bodily passage within which the device is intended to be used. Example materials considered suitable to form a dissolvable sleeve include, but are not limited to, any suitable material described herein, absorbable materials, absorbable minerals, magnesium, and calcium.

The intraluminal medical devices described herein can be placed (e.g., implanted) in any suitable bodily passage, including arteries, veins, ducts, canals, any bodily passage of the pulmonary system, any bodily passage of the vasculature, any bodily passage of the urological system, any bodily passage of the gastric system, any bodily passage of the cardiovascular system, and any other suitable passage where the control of fluid flow and/or materials through the bodily passage is desired. The intraluminal medical devices described herein are considered particularly advantageous for placement in the esophagus to reduce the occurrence of stomach contents from entering the esophagus. In addition, the intraluminal medical devices described herein are considered advantageous for placement in the vasculature, bile duct, and portions of the urinary system, such as the ureter, to regulate the fluid flow and/or materials through the bodily passages.

For example, it is considered advantageous to place an intraluminal medical device, such as one described herein, along a portion of the length of the esophagus such that the frame is deployed across the esophageal sphincter and the distal end of the intraluminal medical device (e.g., second sleeve end) is disposed within the stomach when the intraluminal medical device is in the extended position. This advantageously allows for materials to pass into the stomach when the second sleeve end is in the first configuration and reduces the likelihood of the stomach contents from entering the esophagus when the second sleeve end is in a second, sealed, configuration. When sufficient pressure is placed on a portion, or the entirety, of the sleeve (e.g., during vomiting), the sleeve moves to the inverted position, allowing for the contents of the stomach, or a portion thereof, to move through the sleeve and the esophagus. Subsequently, the sleeve can be moved from the inverted position to the extended position by passing a material (e.g., water) through the esophagus and the intraluminal medical device towards the stomach. A structural feature can be included in an intraluminal medical device that facilitates self reversion of the sleeve, such as a spring or a material with desirable properties.

While the intraluminal medical device has been described as positioned in a particular location, the intraluminal medical device can be positioned at any suitable point along the length of the esophagus, and skilled artisans will be able to select a suitable position along the length of the esophagus based on various considerations, including the desired location of the distal end of an intraluminal medical device. Example locations considered suitable to position an intraluminal medical device include, but are not limited to, positioning an intraluminal medical device such that the distal end of the intraluminal medical device (e.g., second sleeve end) is disposed within the esophagus, positioning an intraluminal medical device such that the distal end of the intraluminal medical device (e.g., second sleeve end) is disposed within the esophageal sphincter, and positioning an intraluminal medical device such that the distal end of the intraluminal medical device (e.g., second sleeve end) is disposed within the stomach.

The inventors have determined that the wall thickness of a sleeve has a direct correlation with the pressure required to invert a sleeve (e.g., inversion pressure), when inversion is a desired characteristic of a sleeve (e.g., in cylindrical sleeves this is correlated with hoop stress). For example, under certain pressures the second sleeve second end will seal, or substantially seal, in order to create a pressure gradient where the pressure distal to the second sleeve end is greater than the pressure proximal to the second sleeve end. Once a pressure gradient is created the sleeve can invert. The inventors have determined that a reduction in the inversion area—the amount of a sleeve adapted to invert into the lumen of a frame—results in an increase in the pressure required to invert the sleeve. In addition, the inventors have determined that an increase in the wall thickness and/or axial length of a sleeve results in an increase in the pressure required to invert a sleeve.

Alternatively, when a sleeve is adapted to only partially invert, the sleeve first end, the sleeve second end, or a combination of the sleeve first end and the sleeve second end, can be adapted to prevent the entire axial length of the sleeve, or a portion thereof, from inverting into the frame. This can be accomplished, for example, by configuring the sleeve to have a sleeve second end that has a first wall thickness that is greater than a second wall thickness at the sleeve first end. Alternatively, this configuration can be accomplished by incorporating a second material (e.g., shape memory material, nitinol) into the sleeve first end, sleeve second end, and/or a portion of the sleeve between the sleeve first end and the sleeve second end that is different than a first material forming the sleeve. This configuration is considered advantageous at least because it reduces the amount of pressure released when the sleeve is in the inverted position and prior to the sleeve second opening moving from the second configuration to the first configuration.

The inventors have also determined that there is a direct correlation between the wall thickness of the sleeve, or a portion thereof, and the volume of fluid and/or material required to revert the sleeve to the extended position from the inverted position (e.g., reversion volume). For example, a sleeve having a first wall thickness that less than a sleeve having a second, greater, wall thickness requires a smaller amount of material and/or fluid to move the sleeve from the inverted position to the extended position. Alternative to requiring a material and/or fluid to revert the sleeve, including a sleeve having a greater wall thickness on a portion of the circumferential length and/or axial length of the sleeve can enable the sleeve to self-revert. This can be accomplished, for example, by including a greater wall thickness (e.g., ridge, wedge, strip, or any region that incorporates an area having a thickness greater than a thickness of an area in another region) on a portion of the axial length and/or circumferential length of a sleeve (e.g., the sleeve second end).

Optionally, sleeve 14 can be formed such that it is biased to the extended position. Biasing a sleeve can be accomplished using any suitable method and or structure, and skilled artisans will be able to select a suitable method and/or structure to bias a sleeve according to a particular embodiment based on various considerations, including the length of the sleeve, the thickness of the sleeve, the inversion area of the sleeve, the shape of the sleeve, and/or the material forming the sleeve. An example method of biasing a sleeve includes, but is not limited to, including a sleeve with a first thickness at the sleeve second end that is less than the thickness of the sleeve at the sleeve first end and a portion of the sleeve between the sleeve first end and the sleeve second end. Example methods considered suitable to form a sleeve having a bias to the extended position or the inverted position include, but are not limited to, dipping, electrospinning, extruding, blow molding, heat forming, spraying, weaving, knitting, and braiding.

Alternatively, or in combination with having a sleeve with a first thickness at the sleeve second end that is less than the thickness of the sleeve at the sleeve first end and a portion of the sleeve between the sleeve first end and the sleeve second end, the sleeve can include one or more reinforcing elements formed of a shape memory material (e.g., nitinol) attached to the exterior surface, interior surface, and/or embedded within the wall of the sleeve, along the entire axial length, a portion of the axial length of the sleeve, the entire circumferential length of the sleeve, or a portion of the circumferential length of the sleeve, such that the sleeve is biased to the extended position or inverted position.

FIGS. 3, 3A, 3B, and 4 illustrate a second exemplary intraluminal medical device 110. The intraluminal medical device 110 is similar to the intraluminal medical device 10 illustrated in FIGS. 1, 1A, 1B, 1C, and 2 and described above, except as detailed below. Reference numbers in FIGS. 3, 3A, 3B, and 4 refer to the same structural element or feature referenced by the same number in FIGS. 1, 1A, 1B, 1C, and 2, offset by 100. Thus, the intraluminal medical device 110 comprises a frame 112 and a sleeve 114 attached to the frame 112. The frame 112 and sleeve 114 cooperatively define a device lumen 116 that extends through the length of the intraluminal medical device 110.

In the illustrated embodiment, the first sleeve end 132 is attached to the second frame end 120 using sutures 160. The first portion 146 of the sleeve 114 extends from the first sleeve end 132 towards the second sleeve end 134 along a first portion 137 of the axial length 135 of the sleeve 114 and along a first portion 143 of the circumferential length 141 of the sleeve 114, as illustrated in FIG. 3A. The second portion 148 of the sleeve 114 extends from the second sleeve end 134 towards the first sleeve end 132 along a second portion 139 of the axial length 135 of the sleeve and along the circumferential length 141 of the sleeve 114, as illustrated in FIG. 3B. Along the first portion 137 of the axial length 135 of the sleeve 114, the second portion 148 extends along a second portion 145 of the circumferential length 141 of the sleeve 114, as illustrated in FIG. 3A. Thus, the first wall thickness 150 and the second wall thickness 152 of the sleeve 114 are disposed at the point of attachment to frame 112.

It is considered advantageous to attach the first portion 146 of the sleeve 114, which has a first wall thickness 150 greater than the second wall thickness 152, to the frame 112 to control the amount of pressure required to move the sleeve 114 from an extended position to an inverted position, and vice versa. For example, the first sleeve end 132 having a first portion 143 of the circumferential length 141 having a first wall thickness 150 allows for the sleeve 114 to move from the extended position to the inverted position, and vice versa, with the application of a greater amount of pressure as compared to a first sleeve end 132 having a circumferential length 141 with a second wall thickness 152.

While the first portion 146 has been described and illustrated as extending along a first portion 137 of the axial length 135 and along a first portion 143 of the circumferential length 141 of sleeve 114, any suitable axial length and/or circumferential length, including the entire axial length and/or circumferential length, can be used. A skilled artisan will be able to select a suitable axial length and/or circumferential length for a first portion according to a particular embodiment based on various considerations, including the desired pressure at which a sleeve moves from an extended position to an inverted position.

In addition, while the second portion 148 has been described and illustrated as extending along the axial length 135 and along a second portion 145 of the circumferential length 141 of sleeve 114 along the first portion 137 of the axial length 135, any suitable axial length and/or circumferential length, including the entire axial length and/or circumferential length, can be used. A skilled artisan will be able to select a suitable axial length and/or circumferential length for a second portion according to a particular embodiment based on various considerations, including the desired pressure at which a sleeve moves from an extended position to an inverted position.

Any suitable combination of axial lengths and/or circumferential lengths can be used for a first portion and/or a second portion, and skilled artisans will be able to select a suitable combination of axial lengths and/or circumferential lengths for a first portion and/or a second portion according to a particular embodiment based on various considerations, including the desired pressure at which a sleeve moves from an extended position to an inverted position.

Second sleeve end 134 is adapted to have a first configuration, as illustrated in FIG. 3, and a second configuration, as illustrated in FIG. 4. In the first configuration, the second end opening 138 is sealed, or substantially sealed, along a portion, or the entirety, of the circumferential length 141 such that materials (e.g., food) and/or fluid (e.g., water) are prevented from passing through the second end opening 138. In the second configuration, the second end opening 138 is open such that materials and/or fluid can pass through the second end opening 138.

Sleeve 114 is adapted to be invertible from an extended position in which the second end 134 and a part of the first portion 146 are disposed outside of the frame lumen 130 to an inverted position in which the second end 134 and the part of the first portion 146 are disposed within the frame lumen 130. The intraluminal medical device 110 is in a first configuration, illustrated in FIG. 3, when the sleeve 114 is in the extended position and in a second configuration, illustrated in FIG. 4, when the sleeve 114 is in the inverted position.

FIGS. 5, 5A and 5B illustrate a third exemplary intraluminal medical device 210. The intraluminal medical device 210 is similar to the intraluminal medical device 10 illustrated in FIGS. 1, 1A, 1B, 1C, and 2 and described above, except as detailed below. Reference numbers in FIGS. 5, 5A, and 5B refer to the same structural element or feature referenced by the same number in FIGS. 1, 1A, 1B, 1C, and 2, offset by 200. Thus, the intraluminal medical device 210 comprises a frame 212 and a sleeve 214 attached to the frame 212. The frame 212 and sleeve 214 cooperatively define a device lumen 216 that extends through the length of the intraluminal medical device 210. Sleeve 214 is illustrated in the second configuration such that second end opening 238 is open to allow material and/or fluids to pass through send end opening 238.

In the illustrated embodiment, first sleeve end 232 is attached to the second frame end 220. The first portion 246 is disposed on the first sleeve end 232 and extends towards the second sleeve end 234 and the second portion 248 is disposed on the second sleeve end 234 and extends towards the first sleeve end 232. Sleeve 214 defines a continuous, or substantially continuous, taper on the inner sleeve surface 240 and outer sleeve surface 242 along the axial length 235 of sleeve 214. The wall thickness of the sleeve tapers from the first wall thickness 250 at the first sleeve end 232 to the second wall thickness 252 at the second sleeve end 234 and extends from the first sleeve end 232 to the second sleeve end 234. Thus, the first wall thickness 250 tapers to the second wall thickness 252 from the first sleeve end 246 to the second sleeve end 248. As best illustrated in FIGS. 5A and 5B, on any planar section orthogonal to the lengthwise axis of the sleeve 214, the wall thickness is constant, or substantially constant, around the entire circumferential length 241 of the sleeve 214. Alternatively, as indicated above, the wall thickness can vary at one or more locations along the circumferential length and/or axial length of a sleeve. Skilled artisans will be able to select a suitable wall thickness for a sleeve according to a particular embodiment based on various considerations, including the bodily passage within which the device is to be used.

Sleeve 214 is adapted to be invertible from an extended position in which the second end 234 and a part of the first portion 246 are disposed outside of the frame lumen 230 to an inverted position in which the second end 234 and the part of the first portion 246 are disposed within the frame lumen 230.

While the sleeve 214 is described and illustrated as defining a taper on the inner sleeve surface 240 and outer sleeve surface 242, various other methods of tapering a sleeve are considered suitable, and skilled artisans will be able to select a suitable method according to a particular embodiment based on various considerations, including the desired pressure at which the sleeve will move from an expanded position to an inverted position. Example methods considered suitable include, but are not limited to, defining a taper on an outer sleeve surface and having an inner sleeve surface that is parallel, or substantially parallel, to the lengthwise axis of a sleeve, and defining a taper on an inner sleeve surface and having an outer sleeve surface that is parallel, or substantially parallel, to the lengthwise axis of a sleeve. The sleeve in a particular embodiment, though, can have any suitable size, shape and configuration.

It is considered advantageous to include the second portion 248 having a second wall thickness 252 that is less than the first wall thickness 250 on the second sleeve end 234 to provide an increased dynamic response to the sleeve 214 (e.g., during eating) when a pressure is exerted on the second sleeve end 234 and to allow the second sleeve end 234 to seal along its circumferential length. It is also considered advantageous to position the second wall thickness 252 on the second sleeve end 234 to allow the sleeve 214 to move from an expanded position to an inverted position, and vice versa, with a lower amount of applied pressure on the second sleeve end 234. For example, when sufficient pressure is placed on the second sleeve end 234, or other portions of sleeve 214, the sleeve 214 will invert and move from the expanded position to the inverted position.

FIGS. 6, 7, 8, 9, 10, 11, and 12, each illustrate sectional views of alternative sleeves for inclusion in an intraluminal medical device, such as intraluminal medical device 10.

FIG. 6 illustrates a sleeve 314 similar to sleeve 214 illustrated in FIGS. 5, 5A, and 5B, and described above, except as detailed below. Reference numbers in FIG. 6 refer to the same structural element or feature referenced by the same number in FIGS. 5, 5A, and 5B, offset by 100. Thus, sleeve 314 has a first sleeve end 332, a second sleeve end 334, and an axial length 335 that extends from the first sleeve end 332 to the second sleeve end 334. The first sleeve end 332 defines a first end opening 336 and the second sleeve end 334 defines a second end opening 338. The sleeve 314 has an inner sleeve surface 340 and an outer sleeve surface 342 and defines a sleeve lumen 344 that extends from the first sleeve end 332 to the second sleeve end 334. Sleeve 314 is illustrated in the second configuration such that second end opening 338 is open to allow material and/or fluids to pass through send end opening 438.

In the illustrated embodiment, sleeve 314 has a first portion 346 having a first wall thickness 350, a second portion 347 having a second wall thickness 351, and a third portion 348 having a third wall thickness 352. The second portion 347 is disposed between the first portion 346 and the third portion 348. Each of the first wall thickness 350, second wall thickness 351, and third wall thickness 352 extends from the inner sleeve surface 340 to the outer sleeve surface 342.

The first portion 346 extends from the first sleeve end 332 towards the second sleeve end 334 to the proximal end of the second portion 347 along a first portion 354 of the axial length 335 of sleeve 314. The first portion 346 defines a taper on the inner sleeve surface 340 and the outer sleeve surface 342 that extends along the first portion 354 of the axial length 335 of sleeve 314. The taper transitions the first wall thickness 350 disposed at the first sleeve end 332 to the second wall thickness 351 at the proximal end of the second portion 347. Thus, the first portion 346 has a wall thickness that tapers from the first sleeve end 332 to the proximal end of the second portion 347. While the illustrated embodiment includes a taper that transitions from the first wall thickness 350 to the second wall thickness 351, any suitable structural transition between two wall thicknesses can be included in a sleeve of an intraluminal medical device according to a particular embodiment. Indeed, the sleeve can include a thickness that can increase or decrease in any direction. Thus, the sleeve thickness can increase or decrease in a proximal direction, a distal direction, along a longitudinal path on the sleeve, along a circumferential path along the sleeve, or along any suitable path on the sleeve.

The second portion 347 extends from the distal end of the first portion 346 towards the second sleeve end 334 to the proximal end of the third portion 348. The second portion 347 defines a continuous, or substantially continuous, second wall thickness 351 that extends along a second portion 355 of the axial length 335 of sleeve 314.

The third portion 348 extends from the distal end of the second portion 347 to the second sleeve end 334. The third portion 348 defines a continuous, or substantially continuous, third wall thickness 352 that extends along a third portion 356 of the axial length 335 of sleeve 314.

The second wall thickness 351 and the third wall thickness 352 are different from one another. In the illustrated embodiment, the second wall thickness 351 is greater than the third wall thickness 352. Thus, the sleeve 314 defines a shoulder 370 at the location where the second portion 347 and the third portion 348 meet. While the second wall thickness 351 has been illustrated and described as greater than the third wall thickness 352, other wall thicknesses are considered suitable, and skilled artisans will be able to select a suitable wall thickness for a particular embodiment based on various considerations, such as the bodily passage within which the device will be used. An example thickness considered suitable includes, but is not limited to, a second wall thickness that is less than a third wall thickness.

In the illustrated embodiment, on any planar section orthogonal to the lengthwise axis of the sleeve 314, the wall thickness of sleeve 314 is constant, or substantially constant, around the entire circumferential length of the sleeve 314. Alternatively, as indicated above, the wall thickness can vary at one or more locations along the circumferential length and/or axial length of a sleeve. Skilled artisans will be able to select a suitable wall thickness for a sleeve according to a particular embodiment based on various considerations, including the bodily passage within which the device is to be used.

Figure 7:
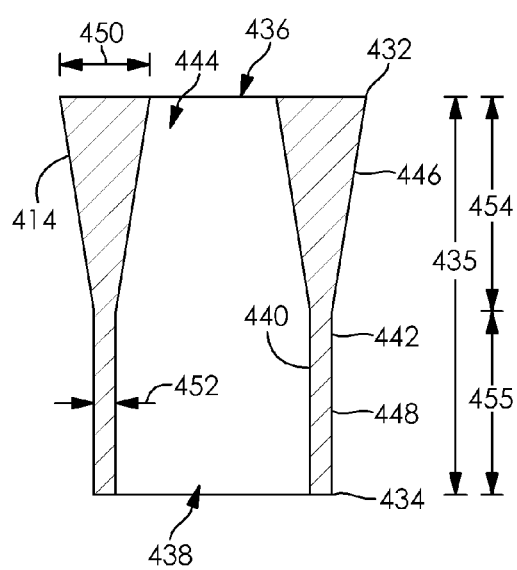
FIG. 7 is a sectional view of a second alternative sleeve for inclusion in an intraluminal medical device.

FIG. 7 illustrates a sleeve 414 similar to sleeve 214 illustrated in FIGS. 5, 5A, and 5B, and described above, except as detailed below. Reference numbers in FIG. 7 refer to the same structural element or feature referenced by the same number in FIGS. 5, 5A, and 5B, offset by 200. Thus, sleeve 414 has a first sleeve end 432, a second sleeve end 434, and an axial length 435 that extends from the first sleeve end 432 to the second sleeve end 434. The first sleeve end 432 defines a first end opening 436 and the second sleeve end 434 defines a second end opening 438. The sleeve 414 has an inner sleeve surface 440 and an outer sleeve surface 442 and defines a sleeve lumen 444 that extends from the first sleeve end 432 to the second sleeve end 434. Sleeve 414 is illustrated in the second configuration such that second end opening 438 is open to allow material and/or fluids to pass through send end opening 438.

In the illustrated embodiment, sleeve 414 has a first portion 446 having a first wall thickness 450 and a second portion 448 having a second wall thickness 452. Each of the first wall thickness 450 and second wall thickness 452 extends from the inner sleeve surface 440 to the outer sleeve surface 442.

The first portion 446 extends from the first sleeve end 432 towards the second sleeve end 434 to the proximal end of the second portion 448 along a first portion 454 of the axial length 435 of sleeve 414. The first portion 446 defines a taper on the inner sleeve surface 440 and outer sleeve surface 442 that extends along the first portion 454 of the axial length 435 of sleeve 414. The taper transitions the first wall thickness 450 disposed at the first sleeve end 432 to the second wall thickness 452 at the proximal end of the second portion 448. Thus, the first portion 446 has a wall thickness that tapers from the first sleeve end 432 to the proximal end of the second portion 447. In an alternative embodiment, a sleeve of an intraluminal medical device has an opposite structural arrangement.

The second portion 447 extends from the distal end of the first portion 446 to the second sleeve end 434. The second portion 447 defines a continuous, or substantially continuous, second wall thickness 452 that extends along a second portion 455 of the axial length 435 of sleeve 414.

In the illustrated embodiment, on any planar section orthogonal to the lengthwise axis of the sleeve 414, the wall thickness of sleeve 414 is constant, or substantially constant, around the entire circumferential length of the sleeve 414. Alternatively, as indicated above, the wall thickness can vary at one or more locations along the circumferential length and/or axial length of a sleeve. Skilled artisans will be able to select a suitable wall thickness for a sleeve according to a particular embodiment based on various considerations, including the bodily passage within which the device is to be used.

Figure 8:
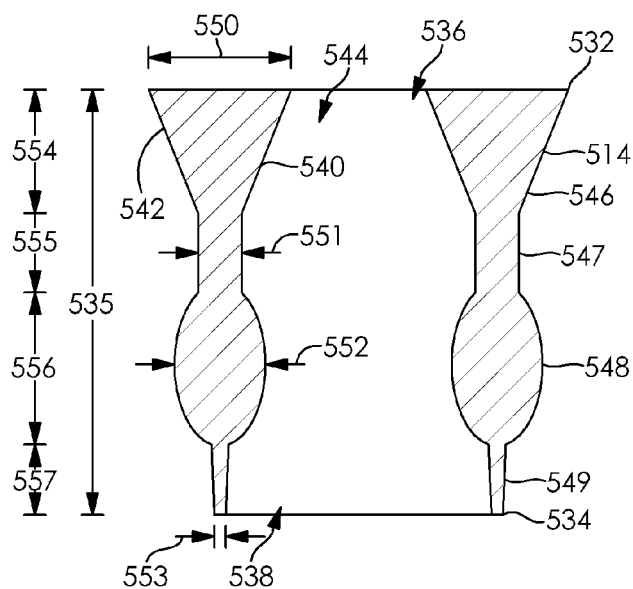
FIG. 8 is a sectional view of a third alternative sleeve for inclusion in an intraluminal medical device.

FIG. 8 illustrates a sleeve 514 similar to sleeve 214 illustrated in FIGS. 5, 5A, and 5B, and described above, except as detailed below. Reference numbers in FIG. 8 refer to the same structural element or feature referenced by the same number in FIGS. 5, 5A, and 5B, offset by 300. Thus, sleeve 514 has a first sleeve end 532, a second sleeve end 534, and an axial length 535 that extends from the first sleeve end 532 to the second sleeve end 534. The first sleeve end 532 defines a first end opening 536 and the second sleeve end 534 defines a second end opening 538. The sleeve 514 has an inner sleeve surface 540 and an outer sleeve surface 542 and defines a sleeve lumen 544 that extends from the first sleeve end 532 to the second sleeve end 534. Sleeve 414 is illustrated in the second configuration such that second end opening 438 is open to allow material and/or fluids to pass through send end opening 438.

In the illustrated embodiment, sleeve 514 has a first portion 546 having a first wall thickness 550, a second portion 547 having a second wall thickness 551, a third portion 548 having a third wall thickness 552, and a fourth portion 549 having a fourth wall thickness 553. Each of the first wall thickness 550, second wall thickness 551, third wall thickness 552, and fourth wall thickness 553 extends from the inner sleeve surface 540 to the outer sleeve surface 542.

The first portion 546 extends from the first sleeve end 532 towards the second sleeve end 534 to the proximal end of the second portion 547 along a first portion 554 of the axial length 535 of sleeve 514. The first portion 546 defines a taper on the inner sleeve surface 540 and the outer sleeve surface 542 that extends along the first portion 554 of the axial length 535 of sleeve 514. The taper transitions the first wall thickness 550 disposed at the first sleeve end 532 to the second wall thickness 551 at the proximal end of the second portion 547. Thus, the first portion has a wall thickness that tapers from the first sleeve end 532 to the proximal end of the second portion 547.

The second portion 547 is disposed between the first portion 546 and the third portion 548 and extends along a second portion 555 of the axial length 535 of sleeve 514. The second portion 547 extends from the distal end of the first portion 546 towards the second sleeve end 534 to the proximal end of the third portion 548. The second wall thickness 551 is continuous, or substantially continuous, along the second portion 555 of the axial length 535.

The third portion 548 is disposed between the second portion 547 and the fourth portion 549 and extends along extends along a third portion 556 of the axial length 535 of sleeve 514. The third portion 548 extends from the distal end of the second portion 547 towards the second sleeve end 534 to the proximal end of the fourth portion 549. The third portion 548 defines an arc on the inner sleeve surface 540 and the outer sleeve surface 542. The third wall thickness 552 increases from the distal end of the second portion 547 to a point along the third portion 556 of the axial length 535 and decreases from the same point, or a different, point, along the third portion 556 of the axial length 535 to the proximal end of the fourth portion 534.

The fourth portion 549 extends from the distal end of the third portion 548 to the second sleeve end 534. The fourth portion 549 defines a taper on the inner sleeve surface 540 and the outer sleeve surface 542 that extends along a fourth portion 557 of the axial length 535 of sleeve 514. The taper transitions the wall thickness of the fourth portion 549 from the wall thickness at the distal end of the third portion 548 to the fourth wall thickness 553 at the second sleeve end 534. Thus, the fourth portion 549 has a wall thickness that tapers from the distal end of the third portion 548 to the second sleeve end 534.

In the illustrated embodiment, on any planar section orthogonal to the lengthwise axis of the sleeve 514, the wall thickness is constant, or substantially constant, around the entire circumferential length of the sleeve 514. Alternatively, as indicated above, the wall thickness can vary at one or more locations along the circumferential length and/or axial length of a sleeve. Skilled artisans will be able to select a suitable wall thickness for a sleeve according to a particular embodiment based on various considerations, including the bodily passage within which the device is to be used.

Figure 9:
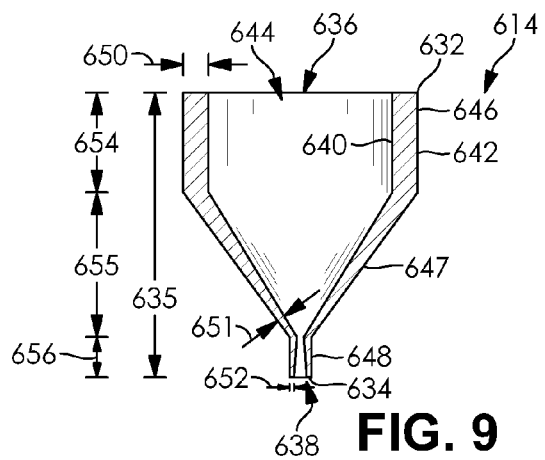
FIG. 9 is a sectional view of a fourth alternative sleeve for inclusion in an intraluminal medical device.

FIG. 9 illustrates a sleeve 614 similar to sleeve 314 illustrated in FIG. 6, and described above, except as detailed below. Reference numbers in FIG. 9 refer to the same structural element or feature referenced by the same number in FIG. 6, offset by 400. Thus, sleeve 614 has a first sleeve end 632, a second sleeve end 634, and an axial length 635 that extends from the first sleeve end 632 to the second sleeve end 634. The first sleeve end 632 defines a first end opening 636 and the second sleeve end 634 defines a second end opening 638. The sleeve 614 has an inner sleeve surface 640 and an outer sleeve surface 642 and defines a sleeve lumen 644 that extends from the first sleeve end 632 to the second sleeve end 634. Sleeve 614 is illustrated in the first sealed, or substantially sealed, configuration.

In the illustrated embodiment, sleeve 614 has a first portion 646 having a first wall thickness 650, a second portion 647 having a second wall thickness 651, and a third portion 648 having a third wall thickness 652. The second portion 647 is disposed between the first portion 646 and the third portion 648. Each of the first wall thickness 650, second wall thickness 651, and third wall thickness 652 extends from the inner sleeve surface 640 to the outer sleeve surface 642.

The first portion 646 extends from the first sleeve end 632 towards the second sleeve end 634 to the proximal end of the second portion 647. The first portion 646 defines a continuous, or substantially continuous, first wall thickness 650 that extends along a first portion 654 of the axial length 635 of sleeve 614.

The second portion 647 extends from the distal end of the first portion 646 towards the second sleeve end 634 to the proximal end of the third portion 648 along a second portion 655 of the axial length 635 of sleeve 614. The second portion 647 defines a taper on the inner sleeve surface 640 that extends along the second portion 655 of the axial length 635 of sleeve 614. The wall thickness of the second portion 647 disposed at the distal end of the first portion 646 transitions from first wall thickness 650 to the second wall thickness 651 at the proximal end of the third portion 648. Thus, the second portion 647 has a wall thickness that tapers from the distal end of the first portion 646 to the proximal end of the third portion 648.

The third portion 648 extends from the distal end of the second portion 647 to the second sleeve end 634 along a third portion 656 of the axial length of sleeve 614. The third portion 648 defines a taper on the inner sleeve surface 640 that extends along the third portion 656 of the axial length 635 of sleeve 614. The wall thickness of the third portion 648 transitions from the second wall thickness 651 at the distal end of the second portion 647 to the third wall thickness 652 at the second sleeve end 634. Thus, the wall thickness of the third portion 648 tapers from the distal end of the second portion 647 to the second sleeve end 634.

In the illustrated embodiment, the wall thickness of sleeve 614 decreases from the distal end of the first portion 646 to the second sleeve end 634. This structural configuration is considered advantageous at least because it allows for sleeve 614 to maintain a second sealed, or substantially sealed, configuration, with the application of a lower amount of pressure as compared to a sleeve having a greater wall thickness at the second portion and/or third portion.

Figure 10:
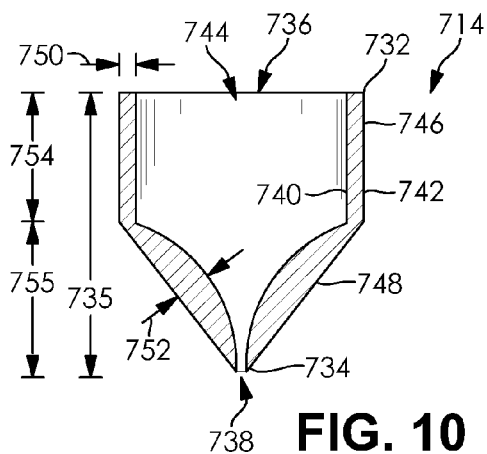
FIG. 10 is a sectional view of a fifth alternative sleeve for inclusion in an intraluminal medical device.

FIG. 10 illustrates a sleeve 714 similar to sleeve 414 illustrated in FIG. 7, and described above, except as detailed below. Reference numbers in FIG. 10 refer to the same structural element or feature referenced by the same number in FIG. 7 offset by 300. Thus, sleeve 714 has a first sleeve end 732, a second sleeve end 734, and an axial length 735 that extends from the first sleeve end 732 to the second sleeve end 734. The first sleeve end 732 defines a first end opening 736 and the second sleeve end 734 defines a second end opening 738. The sleeve 714 has an inner sleeve surface 740 and an outer sleeve surface 742 and defines a sleeve lumen 744 that extends from the first sleeve end 732 to the second sleeve end 734. Sleeve 714 is illustrated in the first sealed, or substantially sealed, configuration.

In the illustrated embodiment, sleeve 714 has a first portion 746 having a first wall thickness 750 and a second portion 748 having a second wall thickness 752. Each of the first wall thickness 750 and second wall thickness 752 extends from the inner sleeve surface 740 to the outer sleeve surface 742.

The first portion 746 extends from the first sleeve end 732 towards the second sleeve end 734 to the proximal end of the second portion 748. The first portion 746 defines a continuous, or substantially continuous, first wall thickness 750 that extends along a first portion 754 of the axial length 735.

The second portion 748 extends from the proximal end of the first portion 746 to the sleeve second end 734 along a second portion 755 of the axial length 735 of sleeve 714. The second portion 748 defines a curve on the inner sleeve surface 740 such that the second wall thickness 752 increases from the distal end of the first portion 746 to a point along the second portion 755 of the axial length 735 and decreases from the same point, or a different point, along the third portion 755 of the axial length 735 to the sleeve second end 734. Thus, the second wall thickness 752 is unevenly distributed along the second portion 755 of the axial length of sleeve 714 such that at a first point along the second portion 755 of the axial length 735 the second portion has a wall thickness having a first length and at a second, different, point along the second portion 755 of the axial length 735 the second portion has a wall thickness having a second length, which is different than the first length.

This structural configuration is considered advantageous at least because it provides a mechanism for positioning the location at which a sleeve will invert upon the application of pressure and the amount of sleeve capable of inversion. For example, this configuration is considered advantageous at least for use in intraluminal medical devices in which a partially invertible sleeve is desired.

Figure 11:
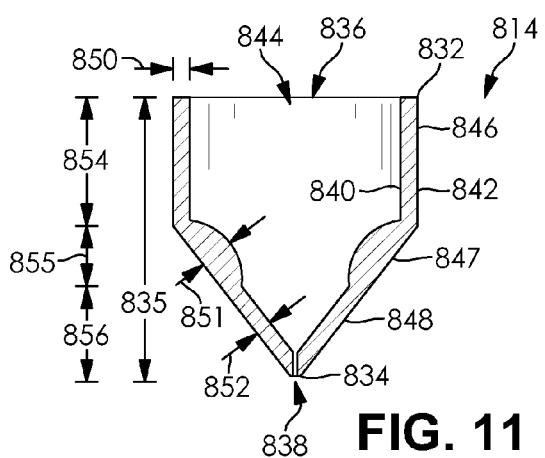
FIG. 11 is a sectional view of a sixth alternative sleeve for inclusion in an intraluminal medical device.

FIG. 11 illustrates a sleeve 814 similar to sleeve 314 illustrated in FIG. 6, and described above, except as detailed below. Reference numbers in FIG. 11 refer to the same structural element or feature referenced by the same number in FIG. 6, offset by 500. Thus, sleeve 814 has a first sleeve end 832, a second sleeve end 834, and an axial length 835 that extends from the first sleeve end 832 to the second sleeve end 834. The first sleeve end 832 defines a first end opening 836 and the second sleeve end 834 defines a second end opening 838. The sleeve 814 has an inner sleeve surface 840 and an outer sleeve surface 842 and defines a sleeve lumen 844 that extends from the first sleeve end 832 to the second sleeve end 834. Sleeve 814 is illustrated in the first sealed, or substantially sealed, configuration.

In the illustrated embodiment, sleeve 814 has a first portion 846 having a first wall thickness 850, a second portion 847 having a second wall thickness 851, and a third portion 848 having a third wall thickness 852. The second portion 847 is disposed between the first portion 846 and the third portion 848. Each of the first wall thickness 850, second wall thickness 851, and third wall thickness 852 extends from the inner sleeve surface 840 to the outer sleeve surface 842.

The first portion 846 extends from the first sleeve end 832 towards the second sleeve end 834 to the proximal end of the second portion 847. The first portion 846 defines a continuous, or substantially continuous, first wall thickness 850 that extends along a first portion 854 of the axial length 835 of sleeve 814.

The second portion 847 extends from the distal end of the first portion 846 to the proximal end of the third portion 848 along a second portion 855 of the axial length 835 of sleeve 814. The second portion 847 defines a curve on the inner sleeve surface 840 such that the second wall thickness 851 increases from the distal end of the first portion 846 to a point along the second portion 855 of the axial length 835 and decreases from the same point, or a different point, along the second portion 855 of the axial length 835 to the proximal end of the third portion 848. Thus, the second wall thickness 851 between the distal end of the first portion 846 and the proximal end of the third portion 848 is greater than the first wall thickness 850 and third wall thickness 852.

The third portion 848 extends from the distal end of the second portion 847 to the second sleeve end 834. The third portion 848 defines a continuous, or substantially continuous, third wall thickness 852 that extends along a third portion 856 of the axial length 835 of sleeve 814.

This structural configuration is considered advantageous at least because it provides a mechanism for positioning the location at which a sleeve will invert upon the application of pressure and the amount of sleeve capable of inversion. For example, the distal end of the second portion can be positioned as desired to control the length of sleeve that inverts into a frame. For example, this configuration is considered advantageous at least for use in intraluminal medical devices in which a partially invertible sleeve is desired.

Figure 12:
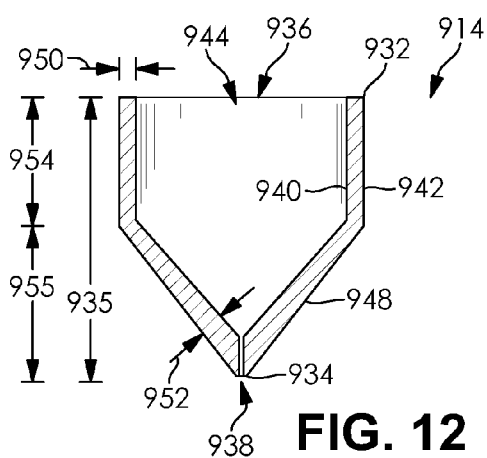
FIG. 12 is a sectional view of a seventh alternative sleeve for inclusion in an intraluminal medical device.

FIG. 12 illustrates a sleeve 914 similar to sleeve 714 illustrated in FIG. 10, and described above, except as detailed below. Reference numbers in FIG. 12 refer to the same structural element or feature referenced by the same number in FIG. 10 offset by 200. Thus, sleeve 914 has a first sleeve end 932, a second sleeve end 934, and an axial length 935 that extends from the first sleeve end 932 to the second sleeve end 934. The first sleeve end 932 defines a first end opening 936 and the second sleeve end 934 defines a second end opening 938. The sleeve 914 has an inner sleeve surface 940 and an outer sleeve surface 942 and defines a sleeve lumen 944 that extends from the first sleeve end 932 to the second sleeve end 934. Sleeve 914 is illustrated in the first sealed, or substantially sealed, configuration.

In the illustrated embodiment, sleeve 914 has a first portion 946 having a first wall thickness 950 and a second portion 948 having a second wall thickness 952. Each of the first wall thickness 950 and second wall thickness 952 extends from the inner sleeve surface 940 to the outer sleeve surface 942.

The first portion 946 extends from the first sleeve end 932 towards the second sleeve end 934 to the proximal end of the second portion 948. The first portion 946 defines a continuous, or substantially continuous, first wall thickness 950 that extends along a first portion 954 of the axial length 935.

The second portion 948 extends from the distal end of the first portion 946 to the sleeve second end 934 along a second portion 955 of the axial length 935 of sleeve 914. The second portion 948 defines a taper on the inner sleeve surface 940 that extends along the second portion 955 of the axial length 935 of sleeve 914. The wall thickness of the second portion 948 increases from the first wall thickness 950 at the distal end of the first portion 946 to the second wall thickness 952 at the second sleeve end 934. Thus, the second portion 948 has a wall thickness that tapers from the second sleeve end 934 to the distal end of the first portion 946.

Figures 13, 13A:
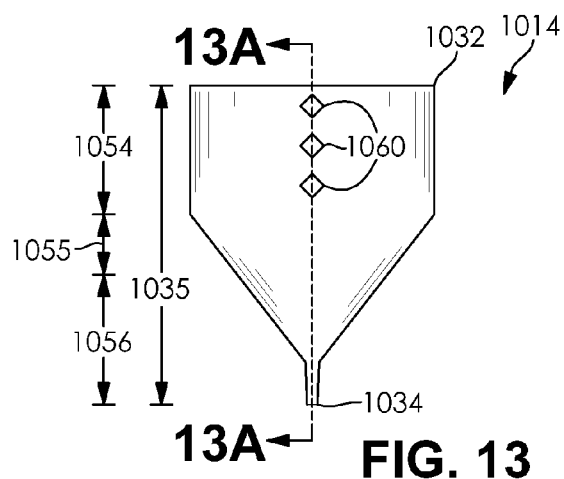
FIG. 13 is a side view of an eighth alternative sleeve for inclusion in an intraluminal medical device.
FIG. 13A is a sectional view of the sleeve illustrated in FIG. 13, taken along line 13A-13A.

FIGS. 13 and 13A illustrate a sleeve 1014 similar to sleeve 314 illustrated in FIG. 6, and described above, except as detailed below. Reference numbers in FIGS. 13 and 13A refer to the same structural element or feature referenced by the same number in FIG. 6, offset by 700. Thus, sleeve 1014 has a first sleeve end 1032, a second sleeve end 1034, and an axial length 1035 that extends from the first sleeve end 1032 to the second sleeve end 1034. The first sleeve end 1032 defines a first end opening 1036 and the second sleeve end 1034 defines a second end opening 1038. The sleeve 1014 has an inner sleeve surface 1040 and an outer sleeve surface 1042 and defines a sleeve lumen 1044 that extends from the first sleeve end 1032 to the second sleeve end 1034. Sleeve 1014 is illustrated in the first sealed, or substantially sealed, configuration. While FIGS. 13 and 13A illustrate an intraluminal medical device according to a particular embodiment, it is understood that a sleeve in a particular embodiment can have any suitable size, shape and configuration.

In the illustrated embodiment, sleeve 1014 has a first portion 1046 having a first wall thickness 1050, a second portion 1047 having a second wall thickness 1051, and a third portion 1048 having a third wall thickness 1052. The second portion 1047 is disposed between the first portion 1046 and the third portion 1048. Each of the first wall thickness 1050, second wall thickness 1051, and third wall thickness 1052 extends from the inner sleeve surface 1040 to the outer sleeve surface 1042. Each of the first wall thickness 1050, second wall thickness 1051, and third wall thickness 1052 has a continuous, or substantially continuous, wall thickness.

In the illustrated embodiment, the first portion 1046 extends from the first sleeve end 1032 towards the second sleeve end 1034 to the proximal end of the second portion 1047 along a first portion 1054 of the axial length 1035 of sleeve 1014. First portion 1046 defines a first set of recesses 1058 that extend from the inner sleeve surface 1040 into the wall of the sleeve 1014 and a second set of recesses 1060 that extend from the outer sleeve surface 1042 and into the wall of the sleeve 1014. In the illustrated embodiment, each recess of the first set of recesses 1058 and the second set of recesses 1060 has a diamond-shaped perimeter. It is considered advantageous to include one or more recesses on the inner sleeve surface and/or outer sleeve surface of the first portion of a sleeve at least because this configuration reduces the pressure necessary to move the sleeve from the extended position to the inverted position, and vice versa, as compared to a sleeve that omits the inclusion of one or more recesses on a first portion.

Each recess of the first set of recesses 1058 and second set of recesses 1060 can be formed using any suitable technique and/or method, and skilled artisans will be able to select a suitable technique and/or method to form a recess on a sleeve based on various considerations, including the desired flexibility of the sleeve. Example methods of forming a recess include, but are not limited to, cutting and removing a portion of the wall of a sleeve, or forming a sleeve and omitting the material where a recess is desired to be positioned.

While each recess of the first set of recesses 1058 and the second set of recesses 1060 has been described as having a diamond-shaped perimeter, a recess can have any suitable shape and skilled artisans will be able to select a suitable shape for a recess of a sleeve according to a particular embodiment based on various considerations. Example shapes considered suitable for a recess include, but are not limited to, circular, rectangular, triangular, faceted, curved, oval, oblong, and any other shape considered suitable for a particular application.

While three recesses have been illustrated on the inner sleeve surface 1040 and the outer sleeve surface 1042, any suitable number of recess can be included in a sleeve, and skilled artisans will be able to select a suitable number of recesses for a sleeve according to a particular embodiment based on various considerations, including the desired flexibility of the sleeve. Example number of recesses considered suitable for inclusion on an inner sleeve surface and/or an outer sleeve surface include, but are not limited to, one, two, three, four, five, six, seven, eight, nine, ten, a plurality, and any other number considered suitable for a particular application.

While each recess of the first set of recesses 1058 and the second set of recesses 1060 has been illustrated and described as defined on the first portion of sleeve 1014, a recess, or a plurality of recesses, can be defined on any suitable portion of a sleeve. Skilled artisans will be able to select a suitable portion of a sleeve to include one or more recesses according to a particular embodiment based on various considerations, including the desired flexibility of the sleeve. Example portions of a sleeve considered suitable to include one or more recesses include, but are not limited to, a portion that extends from a sleeve first end towards a sleeve second end, a portion that extends from a first point between a sleeve first end and a sleeve second end to a second point distal to the first point and between the sleeve first end and the sleeve second end, and a portion that extends from a sleeve second end towards a sleeve first end.

While various structural arrangements have been described for a sleeve for inclusion in an intraluminal medical device, various other structural arrangements are considered suitable. Skilled artisans will be able to select a suitable structural arrangement for a sleeve according to a particular embodiment based on various considerations, including the desired pressure at which a sleeve moves from an expanded position to an inverted position, and vice versa. Example structural arrangements considered suitable include, but are not limited to, a sleeve having the entirety, or a portion, of the axial length of the sleeve defining a taper, a sleeve having the entirety, or a portion, of the axial length of the sleeve defining a curve, a sleeve having the entirety, or a portion, of the axial length of the sleeve defining one or more curves, a sleeve having the entirety, or a portion, of the axial length of the sleeve defining an arc, a sleeve having the entirety, or a portion, of the axial length of the sleeve defining one or more arcs, and/or a sleeve having a wall that defines one or more shoulders along the axial length of the sleeve.

Any of the herein described structural configurations and/or features of a sleeve can be combined in any suitable manner, and skilled artisans will be able to select suitable structural configurations and/or features to include in a sleeve according to a particular embodiment based on various considerations, including the desired pressure at which a sleeve moves from an expanded position to an inverted position. Example structural arrangements and/or features considered suitable for inclusion in a sleeve include, but are not limited to, those described and/or illustrated with respect to sleeve 14, sleeve 114, sleeve 214, sleeve 314, sleeve 414, sleeve 514, sleeve 614, sleeve 714, sleeve 814, sleeve 914, and sleeve 1014.

Figure 16:
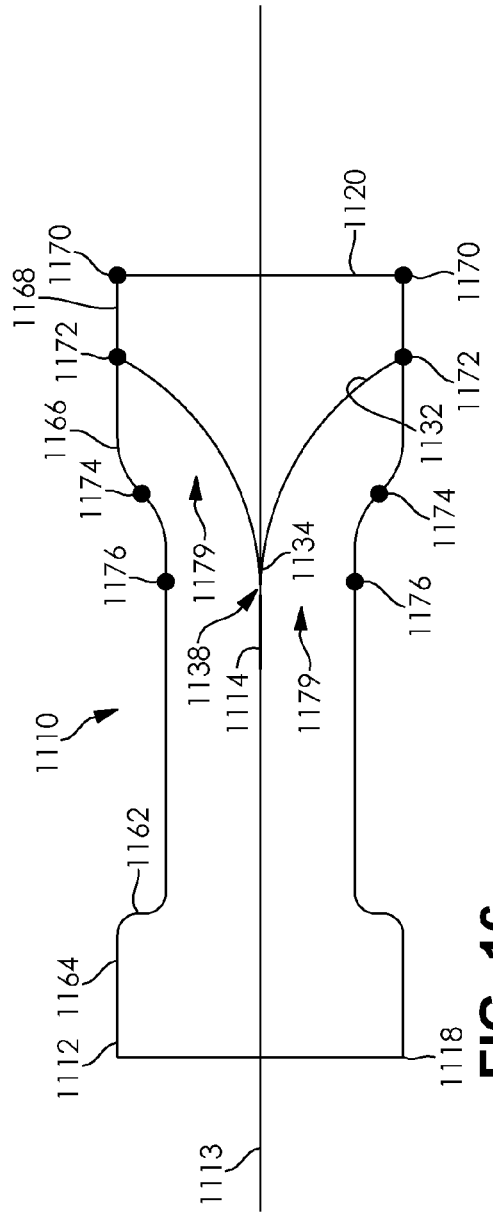
FIG. 16 is a side view of the fourth exemplary intraluminal medical device in the second configuration.

FIGS. 14, 15, and 16 illustrate a fourth exemplary intraluminal medical device 1110. The intraluminal medical device 1110 is similar to the intraluminal medical device 10 illustrated in FIGS. 1, 1A, 1B, 1C, and 2 and described above, except as detailed below. Reference numbers in FIGS. 14, 15, and 16 refer to the same structural element or feature referenced by the same number in FIGS. 1, 1A, 1B, 1C, and 2, offset by 1100. Thus, the intraluminal medical device 1110 comprises a frame 1112 and a sleeve 1114 attached to the frame 1112. The frame 1112 and sleeve 1114 cooperatively define a device lumen 1116 that extends through the length of the intraluminal medical device 1110. Frame 1112 has been illustrated omitting the wire mesh, the plurality of intersecting wire portions, and the plurality of mesh openings for clarity. As described herein, frame can have any suitable structural configuration and be formed of any suitable material.

In the illustrated embodiment, frame 1112 has a lengthwise axis 1113, a first frame end 1118, and a second frame end 1120. The first frame end 1118 defines a first frame end opening 1122 and the second frame end 1120 defines a second frame end opening 1124. The frame 1112 has inner frame surface 1126 and an outer frame surface 1128 and defines a frame lumen 1130 that extends from the first frame end 1118 to the second frame end 1120. The frame 1112 defines a first shoulder 1162 and a first flange 1164 disposed at the proximal end of the frame 1112 and a second shoulder 1166 and a second flange 1168 disposed at the distal end of the frame 1112.

It is considered advantageous to include a first flange 1164 and a second flange 1168 at least because this structural configuration provides a mechanism for maintaining the position of the intraluminal medical device 1110 in a bodily passage (e.g., esophagus) when deployed.

Sleeve 1114 has first sleeve end 1132 that defines a first end opening 1136 and a second sleeve end 1134 defines a second end opening 1138. Second sleeve end 1134 is adapted to have a first configuration, as illustrated in FIGS. 14, 15, and 16, and a second configuration, not shown. In the first configuration, second end opening 1138 is sealed, or substantially sealed, along a portion, or the entirety, of the circumferential length of sleeve 1114 such that materials and/or fluids are prevented from passing through the second end opening 1138. In the second configuration, second end opening 1138 is open such that materials and/or fluid can pass through the second end opening 1138.

In the illustrated embodiment, various sleeve attachment locations 1170, 1172, 1174, and 1176 are illustrated and disposed along the length of frame 1112. Each sleeve attachment location 1170, 1172, 1174, and 1176 is orthogonal to the lengthwise axis 1113 of frame 1112 and extends about a portion, or the entirety, of the circumferential length of frame 1112. Sleeve attachment location 1170 is disposed at the second frame end 1120. Sleeve attachment location 1172 is disposed proximal to second frame end 1120 and distal to second shoulder 1166. Thus, sleeve attachment location 1172 is disposed between second shoulder 1166 and second frame end 1120. Sleeve attachment location 1174 is disposed on second shoulder 1166 and sleeve attachment location 1176 is disposed between first frame end 1118 and second shoulder 1166. Frame 1112 has a different radial strength at each sleeve attachment location 1170, 1172, 1174, and 1176. For example, the radial strength of frame 1112 at sleeve attachment location 1176 is greater than the radial strength of frame 1112 at sleeve attachment location 1174. In addition, the radial strength of frame 1112 at sleeve attachment location 1174 is greater than the radial strength of frame 1112 at sleeve attachment location 1172. Furthermore, the radial strength of frame 1112 at sleeve attachment location 1172 is greater than the radial strength of frame 1112 at sleeve attachment location 1170.

In the illustrated embodiment, first sleeve end 1132 is attached to inner frame surface 1126 at sleeve attachment location 1172 along a portion, or the entirety, of the circumferential length of frame 1112. Thus, first sleeve end 1132 is attached to frame 1112 between the second shoulder 1166 and the second frame end 1120.

FIG. 14 shows sleeve 1114 in an extended position. As shown in FIG. 15, as pressure is applied via a material and/or fluid to sleeve 1114 in a first direction, shown as arrows 1178, sleeve 1114 moves from the extended position to an inverted position, as shown in FIG. 16. As pressure is applied via a material and/or fluid to sleeve 1114 in a second direction, shown as arrows 1179, opposite, or substantially opposite, the first direction 1178, sleeve 1114 moves from the inverted position to the extended position.

While attachment locations 1170, 1172, 1174, and 1176 have been described as orthogonal to the lengthwise axis 1113 of frame 1112, it is considered suitable to attach a sleeve at any suitable angle to the lengthwise axis of a frame. Skilled artisans will be able to select a suitable angle to attach a sleeve to a frame according to a particular embodiment based on various considerations, including the desired pressure at which the sleeve is intended to invert and/or revert. Example angles considered suitable to attach a sleeve on a frame include, but are not limited to, orthogonal to the lengthwise axis of the frame, at an angle between about 1 degree and about 179 degrees relative to the lengthwise axis of the frame, and at any other angle considered suitable for a particular application.

While sleeve 1114 has been described and illustrated as attached to the inner frame surface 1126 at sleeve attachment location 1170, a sleeve can be attached to any suitable surface on a frame and at any suitable location along the axial length of a frame. Skilled artisans will be able to select a suitable surface on a frame and a suitable location on a frame to attach a sleeve according to a particular embodiment based on various considerations, including the materials forming the frame and the sleeve. Example surfaces considered suitable to attach a sleeve to a frame include, but are not, limited to, an inner frame surface, and an outer frame surface. Alternatively, a sleeve can be formed on, or as part of, the frame, as described in more detail herein. Example locations considered suitable to attach a sleeve include, but are not limited to, attachment location 1170, attachment location 1172, attachment location 1174, attachment location 1176, at should 1162, at flange 1164, at shoulder 1166, at flange 1168, at sleeve first end 1118, and any other location along the axial length of a frame considered suitable for a particular application.

Figure 17:
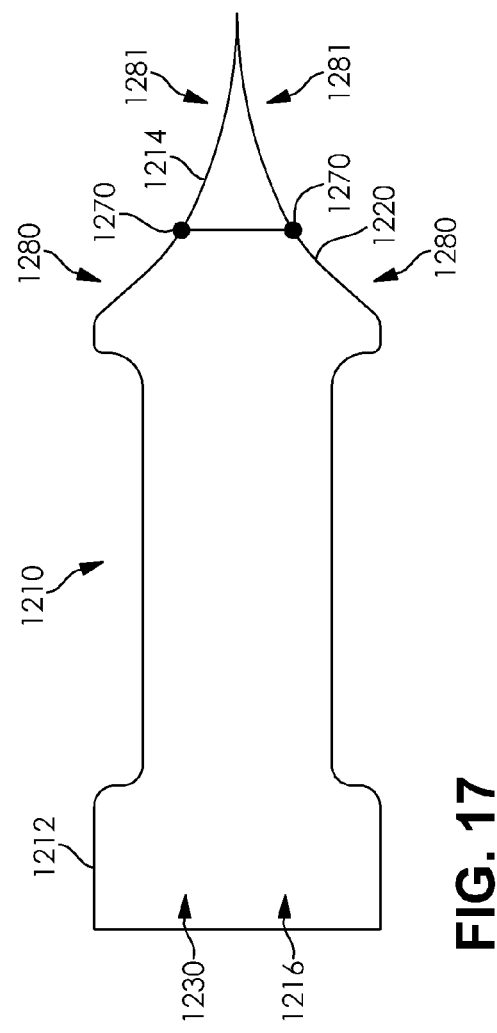
FIG. 17 is a side view of a fifth exemplary intraluminal medical device in a second configuration.

FIG. 17 illustrates a fifth exemplary intraluminal medical device 1210. The intraluminal medical device 1210 is similar to the intraluminal medical device 1110 illustrated in FIGS. 14, 15, and 16 and described above, except as detailed below. Reference numbers in FIG. 17 refer to the same structural element or feature referenced by the same number in FIGS. 14, 15, and 16, offset by 100. Thus, the intraluminal medical device 1210 comprises a frame 1212 and a sleeve 1214 attached to the frame 1212. The frame 1212 and sleeve 1214 cooperatively define a device lumen 1216 that extends through the length of the intraluminal medical device 1210.

In the illustrated embodiment, sleeve 1214 is attached to frame 1112 at sleeve attachment location 1270, which is disposed at frame second end 1220. Frame second end 1220 is adapted to move from a first configuration (e.g., shown in FIG. 16) to a second configuration, shown in FIG. 17 in which frame second end 1220 moves radially inward (e.g., collapses inward) into frame lumen 1230. Frame second end 1220 moves radially inward in response to a first pressure, shown as arrows 1280, being applied to intraluminal medical device 1210. First pressure is less than a second pressure, shown as arrows 1281, required to move sleeve 1214 from the extended position to the inverted position. This structural arrangement is considered advantageous at least because it prevents sleeve 1214 from moving to the inverted position and provides a mechanism for preventing material and/or fluid from passing through the intraluminal medical device through sleeve 1214.

Frame second end 1220 can be adapted to move radially inward any suitable length and at any suitable pressure, and skilled artisans will be able to select a suitable length and a suitable pressure to adapt a frame second end to move radially inward according to a particular embodiment based on various considerations. In addition, frame 1212 can be formed of any suitable material using any suitable method to accomplish movement of frame second end 1220, and skilled artisans will be able to select a suitable material and method to form a frame according to a particular embodiment based on various considerations. Example materials and methods considered suitable include, but are not limited to, those described herein, forming a frame with a lower number of wire portions along the axial length and/or circumferential length of the frame that is to be moveable radially inward as compared to the reminder of the axial length and/or circumferential length of the frame, and any other material and/or method considered suitable for a particular application.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. An implantable medical device, comprising:
an expandable frame having a first frame end and a second frame end and defining a frame lumen extending from the first frame end to the second frame end; and
a sleeve attached to the frame, the sleeve having a first sleeve end, a second sleeve end, a wall, an inner surface, an outer surface, a first portion, a second portion, an axial length extending from the first sleeve end to the second sleeve end, and defining a sleeve lumen extending between the first sleeve end and the second sleeve end, the first portion extending along a portion of the axial length from the first sleeve end towards the second sleeve end, the first portion having a first wall thickness extending between the inner surface and the outer surface, the second portion disposed between the first portion and the second sleeve end and extending along a portion of the axial length from the first portion towards the second sleeve end, the second portion having a second wall thickness extending between the inner surface and the outer surface, the second sleeve end having a third wall thickness extending between the inner surface and the outer surface, the first wall thickness being different than the second wall thickness, the third wall thickness being less than the second wall thickness;
wherein the sleeve is adapted to invert between an extended position in which the second sleeve end and a part of the first portion is disposed outside of the frame lumen and an inverted position in which the second sleeve end and the part of the first portion is disposed within the frame lumen.

2. The implantable medical device of claim 1, wherein the sleeve has a circumferential length; and
wherein the third wall thickness extends along the entire circumferential length of the sleeve.

3. The implantable medical device of claim 1, wherein the sleeve defines a taper along a portion of the axial length of the sleeve.

4. The implantable medical device of claim 1, wherein the sleeve defines a taper along the entire axial length of the sleeve.

5. The implantable medical device of claim 1, wherein the sleeve has a circumferential length; and
wherein the second wall thickness extends along the entire circumferential length of the sleeve.

6. The implantable medical device of claim 1, wherein the second wall thickness is greater than the first wall thickness.

7. The implantable medical device of claim 6, wherein the sleeve has a circumferential length; and
wherein the second wall thickness extends along the entire circumferential length of the sleeve.

8. The implantable medical device of claim 6, wherein the second portion defines a curve on the inner surface of the sleeve that extends into the sleeve lumen.

9. The implantable medical device of claim 8, wherein the curve extends from the first portion to the second sleeve end.

10. The implantable medical device of claim 1, wherein the wall defines a recess that extends from the inner surface of the sleeve and into the wall of the sleeve.

11. The implantable medical device of claim 1, wherein the wall defines a recess that extends from the outer surface of the sleeve and into the wall of the sleeve.

12. An implantable medical device, comprising:
an expandable frame having a first frame end and a second frame end and defining a frame lumen extending from the first frame end to the second frame end; and
a sleeve attached to the frame, the sleeve having a first sleeve end, a second sleeve end, a wall, an inner surface, an outer surface, a first portion, a second portion, a circumferential length, an axial length extending from the first sleeve end to the second sleeve end, and defining a sleeve lumen extending between the first sleeve end and the second sleeve end, the first portion extending along a portion of the axial length from the first sleeve end towards the second sleeve end, the first portion having a first wall thickness extending between the inner surface and the outer surface, the second portion disposed between the first portion and the second sleeve end and extending along a portion of the axial length from the first portion towards the second sleeve end, the second portion having a second wall thickness extending between the inner surface and the outer surface, the second sleeve end having a third wall thickness extending between the inner surface and the outer surface, the first wall thickness being different than the second wall thickness, the second wall thickness extending along the entire circumferential length of the sleeve, the third wall thickness being less than the second wall thickness and extending along the entire circumferential length of the sleeve;
wherein the sleeve is adapted to invert between an extended position in which the second sleeve end and a part of the first portion is disposed outside of the frame lumen and an inverted position in which the second sleeve end and the part of the first portion is disposed within the frame lumen.

13. The implantable medical device of claim 12, wherein the sleeve defines a taper along a portion of the axial length of the sleeve.

14. The implantable medical device of claim 12, wherein the sleeve defines a taper along the entire axial length of the sleeve.

15. The implantable medical device of claim 12, wherein the second wall thickness is greater than the first wall thickness.

16. The implantable medical device of claim 15, wherein the second portion defines a curve on the inner surface of the sleeve that extends into the sleeve lumen.

17. The implantable medical device of claim 16, wherein the curve extends from the first portion to the second sleeve end.

18. The implantable medical device of claim 12, wherein the wall defines a recess that extends from the inner surface of the sleeve and into the wall of the sleeve.

19. The implantable medical device of claim 12, wherein the wall defines a recess that extends from the outer surface of the sleeve and into the wall of the sleeve.

20. An implantable medical device, comprising:
   an expandable frame having a first frame end and a second frame end and defining a frame lumen extending from the first frame end to the second frame end; and
   a sleeve attached to the frame, the sleeve having a first sleeve end, a second sleeve end, a wall, an inner surface, an outer surface, a first portion, a second portion, a circumferential length, an axial length extending from the first sleeve end to the second sleeve end, and defining a sleeve lumen extending between the first sleeve end and the second sleeve end, the first portion extending along a portion of the axial length from the first sleeve end towards the second sleeve end, the first portion having a first wall thickness extending between the inner surface and the outer surface, the second portion disposed between the first portion and the second sleeve end and extending along a portion of the axial length from the first portion towards the second sleeve end, the second portion having a second wall thickness extending between the inner surface and the outer surface, the second sleeve end having a third wall thickness extending between the inner surface and the outer surface, the first wall thickness being different than the second wall thickness, the second wall thickness extending along the entire circumferential length of the sleeve, the third wall thickness being less than the second wall thickness and extending along the entire circumferential length of the sleeve, the wall defining a first recess extending from the inner surface of the sleeve and into the wall of the sleeve, the wall defining a second recess extending from the outer surface of the sleeve and into the wall of the sleeve;
   wherein the sleeve is adapted to invert between an extended position in which the second sleeve end and a part of the first portion is disposed outside of the frame lumen and an inverted position in which the second sleeve end and the part of the first portion is disposed within the frame lumen.

\* \* \* \* \*